(12) United States Patent
Elias et al.

(10) Patent No.: US 11,241,526 B2
(45) Date of Patent: *Feb. 8, 2022

(54) METHOD AND SYSTEM FOR ENHANCED IMAGING VISUALIZATION OF DEEP BRAIN ANATOMY USING INFUSION

(71) Applicant: University of Virginia Patent Foundation, Charlottesville, VA (US)

(72) Inventors: William J. Elias, Charlottesville, VA (US); Aaron E. Bond, Charlottesville, VA (US); George T. Gillies, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 443 days.

This patent is subject to a terminal disclaimer.

(21) Appl. No.: 16/181,498

(22) Filed: Nov. 6, 2018

(65) Prior Publication Data

US 2019/0070356 A1    Mar. 7, 2019

Related U.S. Application Data

(63) Continuation of application No. 14/429,592, filed as application No. PCT/US2013/060404 on Sep. 18, 2013, now Pat. No. 10,159,782.

(Continued)

(51) Int. Cl.
*A61M 5/00* (2006.01)
*A61M 25/10* (2013.01)
(Continued)

(52) U.S. Cl.
CPC ............. *A61M 5/007* (2013.01); *A61B 5/055* (2013.01); *A61B 6/12* (2013.01); *A61B 6/481* (2013.01);
(Continued)

(58) Field of Classification Search
CPC .............. A61M 5/007; A61M 25/0026; A61M 25/007; A61M 25/10; A61M 2025/0037;
(Continued)

(56) References Cited

U.S. PATENT DOCUMENTS

| 2003/0130651 A1* | 7/2003 | Lennox ...................... A61F 7/02 606/21 |
| 2004/0034321 A1* | 2/2004 | Larnard .................. A61F 7/123 604/113 |

(Continued)

*Primary Examiner* — Sanjay Cattungal
(74) *Attorney, Agent, or Firm* — Robert J. Decker

(57) ABSTRACT

Provided is a method and system for delivering a diagnostic agent to a site in the brain of a subject for imaging at least a portion of the brain site on a medical imaging system. The method and system includes a catheter device with associated lumens having diagnostic agent ports for delivering the diagnostic agent (e.g., infusate) through the lumens and advancing the diagnostic agent so as to exit out from the lumens to at least a portion of the brain site and while sealing a portion of the brain site thereby preventing the exited diagnostic agent from travelling proximally beyond the sealing location, and at the same time imaging at least a portion of the brain site during at least a portion of the sealing duration so that the brain site can be visualized on a medical imaging system. The diagnostic agent (infusate) is able to highlight borders and internal patterns of the deep structures of the brain thereby enabling direct targeting. Ultimately this leads to reduced complications, enhanced therapy, and the elimination of the need for awake surgery. The method and system provides the capability heretofore not possible to visualize the small, often indistinct regions, which will greatly improve clinical outcomes with therapeutic interventions.

29 Claims, 12 Drawing Sheets

US 11,241,526 B2
Page 2

Related U.S. Application Data

(60) Provisional application No. 61/874,741, filed on Sep. 6, 2013, provisional application No. 61/703,191, filed on Sep. 19, 2012.

(51) Int. Cl.
| | |
|---|---|
| *A61B 5/055* | (2006.01) |
| *A61M 25/00* | (2006.01) |
| *A61B 6/12* | (2006.01) |
| *A61B 6/00* | (2006.01) |
| *A61N 1/36* | (2006.01) |
| *A61B 5/00* | (2006.01) |
| *A61M 25/01* | (2006.01) |
| *A61M 31/00* | (2006.01) |
| *G01R 33/28* | (2006.01) |
| *A61B 6/03* | (2006.01) |

(52) U.S. Cl.
CPC ........... *A61B 6/501* (2013.01); *A61M 25/007* (2013.01); *A61M 25/0026* (2013.01); *A61M 25/10* (2013.01); *A61N 1/36139* (2013.01); A61B 5/0042 (2013.01); A61B 6/032 (2013.01); A61M 25/0127 (2013.01); A61M 25/1002 (2013.01); A61M 31/005 (2013.01); A61M 2025/0037 (2013.01); A61M 2025/0042 (2013.01); A61M 2025/105 (2013.01); A61M 2025/1052 (2013.01); *A61M 2025/1093* (2013.01); *G01R 33/285* (2013.01)

(58) Field of Classification Search
CPC .......... A61M 25/0127; A61M 25/1002; A61M 31/005; A61M 2025/0042; A61M 2025/105; A61M 2025/1052; A61M 2025/1093; A61N 1/36139; A61B 6/12; A61B 6/481; A61B 6/501; A61B 5/055; A61B 6/032; A61B 5/0042; G01R 33/285
See application file for complete search history.

(56) References Cited

U.S. PATENT DOCUMENTS

| | | | |
|---|---|---|---|
| 2008/0171990 A1* | 7/2008 | Zauner | A61B 5/14553 604/175 |
| 2008/0228140 A1* | 9/2008 | Mittermeyer | A61M 25/0023 604/104 |
| 2010/0114093 A1* | 5/2010 | Mahapatra | A61B 18/1492 606/41 |
| 2010/0145330 A1* | 6/2010 | Badie | A61B 17/32002 606/33 |
| 2012/0171281 A1* | 7/2012 | Spakevicius | A61P 35/00 424/450 |
| 2015/0238685 A1* | 8/2015 | Elias | A61N 1/36139 600/420 |
| 2017/0325685 A1* | 11/2017 | Shachar | A61B 5/031 |

\* cited by examiner

METHOD AND SYSTEM FOR ENHANCED IMAGING VISUALIZATION OF DEEP BRAIN ANATOMY USING INFUSION

RELATED APPLICATIONS

The present application is a continuation application of U.S. application Ser. No. 14/429,592, filed Mar. 19, 2015, which is a national stage filing of International Application No. PCT/US2013/060404, filed Sep. 18, 2013, which claims priority under 35 U.S.C. § 119(e) from U.S. Provisional Application Ser. No. 61/703,191, filed Sep. 19, 2012, entitled "Enhanced Magnetic Resonance Visualization of Deep Brain Anatomy with Stereotactic Convection Infusion(s)," and U.S. Provisional Application Ser. No. 61/874,741, filed Sep. 6, 2013, entitled "Enhanced Magnetic Resonance Visualization of Deep Brain Anatomy with Stereotactic Convection Infusion(s);" the disclosures of which are hereby incorporated by reference herein in their entirety.

TECHNICAL FIELD

The present invention relates generally to the field of medical imaging. More specifically, the present invention also relates to a catheter device used to enhance deep brain magnetic resonance imaging using infusion.

BACKGROUND

Deep Brain anatomy has become the focus of many neurosurgical procedures where precise targeting is paramount for successful interventions of many neurologic disorders. These structures can be very small and indistinct so that even contemporary imaging systems and techniques are limited to demonstrate the anatomy. In particular, the shortcomings of some of the stereotactic neurosurgery targets structures may include the basal ganglia, thalamus, and mesial temporal lobe for therapies utilizing lesioning, stimulation, and infusions of therapeutic compounds.

Current methods in targeting small, deeply located, and indistinct brain structures requires a pre-operative MRI which is then merged with a generic stereotactic atlas to define the targets. Then a lesioning electrode, stimulating electrode, or microcatheter for convection enhanced delivery (CED) is inserted through the skull positioned at the predefined point. However, owing to the variation in the human brain from patient to patient, especially in patients with aging brains, or as a result of brain shift following opening of the skull, there are inherent errors in targeting. Complications, adverse effects, and subtherapeutic results arise when the targeting of these structures is inadequate. As a result, most of the procedures rely on the patient being awake to intraoperatively test the region of interest before delivering a therapeutic treatment.

Many current methods and systems for MRI visualization of deep brain structures do not have the capability to visualize small, often indistinct regions that would otherwise greatly improve clinical outcomes with therapeutic interventions.

In contrast, an aspect of various embodiments of the present invention provides, among other things, the capability heretofore not possible to visualize the small, often indistinct regions, which will greatly improve clinical outcomes with therapeutic interventions.

Many current methods and systems of stereotactic surgeries for interventions cannot reasonably rely on the accuracy of targeting deep brain anatomic structures like the subcortical nuclei.

Overview

It should be appreciated that enabling a patient with a movement disorder from Parkinson's, Essential Tremor, or other underlying etiology to resume normal activities of daily living is life altering and the goal of either pharmacotherapy or surgical therapy in these patients. For patients who have failed pharmacotherapy the only option is surgical. The surgical cures include lesioning, stimulating, and injecting drugs in specific regions of the brain with millimeter accuracy. The current state of the art in delivering these therapies relies on standardized atlases of the human brain overlaid on an MRI. Direct targeting is not possible owing to an inability to directly visualize the tissues of interest or final target. This leads to errors that may require repeat surgery, increased risk of complications, and the need for awake surgery which can be frightening or intolerable to many patients.

An aspect of an embodiment of the present invention provides for, among other things, providing patent protectable technology (systems and devices) and methods which enable direct visualization of these deep brain structures using, for example, convection enhanced delivery (CED) of infusates which highlight borders and internal patterns of these deep structures thereby enabling direct targeting. Ultimately this leads to reduced complications, enhanced therapy, and the elimination of the need for awake surgery.

An aspect of an embodiment of the present invention provides for, among other things, medical imaging, such as is employed for stereotactic neurosurgery for the treatment of chronic neurologic disorders like Parkinson's disease, tremor, epilepsy, neurodegenerative conditions or diseases, Alzheimer's, seizures, paralysis, and psychiatric disease, or the like. The methods employed may further include lesioning, stimulation, and local delivery of drugs, or other medium or devices.

An aspect of an embodiment of the present invention provides for, among other things, deep brain stimulation (DBS) of the globus pallidum or subthalamic nucleus (or other target brain sites) for the surgical treatment of Parkinson's disease or other neurological disorders. The DBS targeting practiced as part of the present invention improves visualization of the critical brain structures as well as the catheter device itself and related components. As such, it assures accurate electrode positioning and anatomy targeting without necessarily requiring the patient/subject to be awake. Similarly, the individual thalamic nuclei can be distinguished with the imaging as disclosed herein.

An aspect of an embodiment of the present invention provides, but not limited thereto, a catheter system for delivering a diagnostic agent to a site in the brain of a subject for imaging at least a portion of the brain site on a medical imaging system. The catheter system may comprise: a catheter device, the catheter device includes as a first lumen, the first lumen having a first lumen proximal region, a first lumen distal regional, and a first lumen longitudinal region there between; the first lumen configured to convey a diagnostic agent within the first lumen, and at least a portion of the first lumen having one or more ports configured to allow the conveyed diagnostic agent to exit from the first lumen to at least a portion of the brain site; and a portion of the catheter device having a cross-sectional area greater than portions of the catheter located proximally so as to define a seal within at least a portion of the brain site, wherein the seal is configured to prevent the exited diagnostic agent from travelling proximally beyond the seal while at least a portion of the brain site can be visualized on a medical imaging system.

An aspect of an embodiment of the present invention provides, but not limited thereto, a method for delivering a diagnostic agent to a site in the brain of a subject for imaging at least a portion of the brain site on a medical imaging system. The method may comprise: providing a catheter device, the catheter device includes as a first lumen, the first lumen having a first lumen proximal region, a first lumen distal regional, and a first lumen longitudinal region there between; at least of a portion of the first lumen having one or more diagnostic agent ports; delivering the diagnostic agent through the first lumen; advancing the diagnostic agent from the first lumen to exit out from the first lumen to at least a portion of the brain site; sealing a portion of the brain site, wherein the sealing prevents the exited diagnostic agent from travelling proximally beyond the sealing location; and imaging at least a portion of the brain site during at least a portion of the sealing duration so that the at least a portion of the brain site can be visualized on a medical imaging system.

An aspect of an embodiment of the present invention provides, but not limited thereto, a catheter system for delivering a diagnostic agent to a site in the brain of a subject for imaging at least a portion of the brain site on a medical imaging system for purpose of treating a neurologic disorder of the subject. The catheter system may comprise: a catheter device, the catheter device includes as a first lumen, the first lumen having a first lumen proximal region, a first lumen distal regional, and a first lumen longitudinal region there between; the first lumen configured to convey a diagnostic agent within the first lumen, and at least a portion of the first lumen having one or more ports configured to allow the conveyed diagnostic agent to exit from the first lumen to at least a portion of the brain site; a portion of the catheter device having a cross-sectional area greater than portions of the catheter located proximally so as to define a seal within at least a portion of the brain site, wherein the seal is configured to prevent the exited diagnostic agent from travelling proximally beyond the seal while at least a portion of the brain site can be visualized on a medical imaging system; and an electrical lead or deep brain simulation (DBS) device at least partially disposed in the first lumen for applying electrical stimulation by use of the electrical lead or DBS, to a site in the brain for providing a DBS.

An aspect of an embodiment of the present invention provides, but not limited thereto, a catheter system for delivering a diagnostic agent to a site in the brain of a subject for imaging at least a portion of the brain site on a medical imaging system for purpose of treating a neurologic disorder of the subject. The catheter system may comprise: a catheter device, the catheter device includes as a first lumen, the first lumen having a first lumen proximal region, a first lumen distal regional, and a first lumen longitudinal region there between; the first lumen configured to convey a diagnostic agent within the first lumen, and at least a portion of the first lumen having one or more ports configured to allow the conveyed diagnostic agent to exit from the first lumen to at least a portion of the brain site; a portion of the catheter device having a cross-sectional area greater than portions of the catheter located proximally so as to define a seal within at least a portion of the brain site, wherein the seal is configured to prevent the exited diagnostic agent from travelling proximally beyond the seal while at least a portion of the brain site can be visualized on a medical imaging system; a second lumen, the second lumen having a second lumen proximal region, a second lumen distal regional, and a second lumen longitudinal region there between; and an electrical lead or deep brain simulation (DBS) device at least partially disposed in the second lumen for applying electrical stimulation by use of the electrical lead or DBS, to a site in the brain for providing a DBS.

An aspect of an embodiment of the present invention provides, but not limited thereto, a method for delivering a diagnostic agent to a site in the brain of a subject for imaging at least a portion of the brain site on a medical imaging system for purpose of treating a neurologic disorder of the subject, the method comprising: providing a catheter device, the catheter device includes as a first lumen, the first lumen having a first lumen proximal region, a first lumen distal regional, and a first lumen longitudinal region there between; at least of a portion of the first lumen having one or more diagnostic agent ports; delivering the diagnostic agent through the first lumen; advancing the diagnostic agent from the first lumen to exit out from the first lumen to at least a portion of the brain site; sealing a portion of the brain site, wherein the sealing prevents or mitigates (or hinders) the exited diagnostic agent from travelling proximally beyond the sealing location; imaging at least a portion of the brain site during at least a portion of the sealing duration so that the at least a portion of the brain site can be visualized on a medical imaging system; delivering an electrical lead or deep brain simulation (DBS) device into the first lumen; and applying electrical stimulation by use of the electrical lead or DBS, to a site in the brain for providing the DBS.

An aspect of an embodiment of the present invention provides, but not limited thereto, a method for delivering a diagnostic agent to a site in the brain of a subject for imaging at least a portion of the brain site on a medical imaging system for purpose of treating a neurologic disorder of the subject. The method may comprise: providing a catheter device, the catheter device includes as a first lumen, the first lumen having a first lumen proximal region, a first lumen distal regional, and a first lumen longitudinal region there between; at least of a portion of the first lumen having one or more diagnostic agent ports; delivering the diagnostic agent through the first lumen; advancing the diagnostic agent from the first lumen to exit out from the first lumen to at least a portion of the brain site; sealing a portion of the brain site, wherein the sealing prevents the exited diagnostic agent from travelling proximally beyond the sealing location; imaging at least a portion of the brain site during at least a portion of the sealing duration so that the at least a portion of the brain site can be visualized on a medical imaging system; the catheter further includes a second lumen, the second lumen having a second lumen proximal region, a second lumen distal regional, and a second lumen longitudinal region there between; delivering an electrical lead or deep brain simulation (DBS) device into the second lumen; and applying electrical stimulation by use of the electrical lead or DBS, to a site in the brain for providing the DBS.

A method and system provided for delivering a diagnostic agent to a site in the brain of a subject for imaging at least a portion of the brain site on a medical imaging system. The method and system includes a catheter device with associated lumens having diagnostic agent ports for delivering the diagnostic agent (e.g., infusate) through the lumens and advancing the diagnostic agent so as to exit out from the lumens to at least a portion of the brain site and while sealing a portion of the brain site thereby preventing the exited diagnostic agent from travelling proximally beyond the sealing location, and at the same time imaging at least a portion of the brain site during at least a portion of the sealing duration so that the brain site can be visualized on a medical imaging system. The diagnostic agent (infusate) is able to highlight borders and internal patterns of the deep structures of the brain thereby enabling direct targeting. Ultimately this leads to reduced complications, enhanced therapy, and the elimination of the need for awake surgery.

These and other objects, along with advantages and features of various aspects of embodiments of the invention disclosed herein, will be made more apparent from the description, drawings and claims that follow.

BRIEF DESCRIPTION OF THE DRAWINGS

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

FIG. 11B provides a partial view of FIG. 11A and which is set at a higher magnification.

DETAILED DESCRIPTION OF EXEMPLARY EMBODIMENTS

Figure 1:
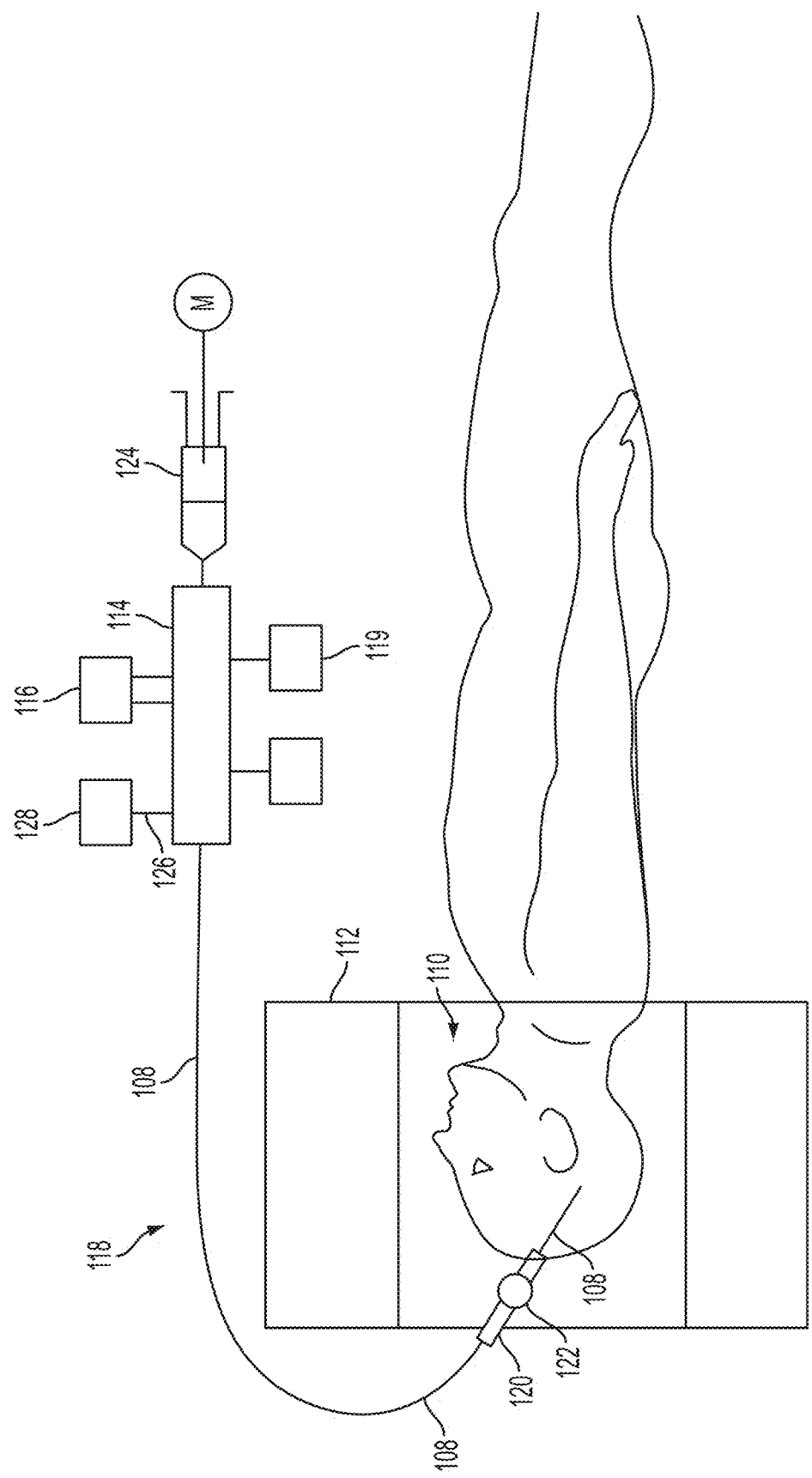
FIG. 1 provides a schematic diagram showing a patient, or any subject or object, undergoing an examination and/or intervention in an MRI system whereby a catheter device is disposed within the patient.

FIG. 1 provides a schematic diagram of an aspect of an embodiment of the present invention showing a patient 110, or any subject or object, undergoing an examination and/or intervention inside the bore of an MRI system 112 whereby a catheter system 118 includes a catheter device 108 that is disposed within the patient 110. It should be appreciated that while an MRI related system is depicted, a variety of systems and methods may implemented within the spirit of the present invention including, but not limited thereto, the following: computed tomography (CT), fluoroscopy, ultrasound, PET scanning, nuclear medicine camera, other radiological systems, or other biomedical imaging techniques and methods. A manifold 114 may couple several therapeutic or diagnostic devices or systems typified by device 116 to the catheter system 118. A syringe, flow-driver and/or pumping device 124 may also be in communication with the manifold 114. The catheter device 108 in turn may be delivered through a guide sheath 120 that may be positioned in a navigation guide 122. In operation the physician or user inserts the catheter device 108 into the brain (or other anatomy part or subject region) under MRI guidance or other applicable examination or intervention. The same or similar MRI visualization may be used to follow the progress of the implant both acutely and chronically. This specific version of the catheter within the concepts disclosed herein may have an outer catheter/tube with an inner catheter/tube within that will be described in greater detail herein. This catheter device may have various interior and peripheral lumens, chambers, conduits, and channels that will also be discussed in greater detail herein, within the context of the disclosure provided. Such interior and peripheral lumens, chambers, conduits, and channels may be used to deliver other devices and perform various diagnostic functions. For example, each lumen, chamber, conduits, and channel may communicate with a separate port of the manifold 114. A lumen, chamber, conduit, or channel may contain a pressure transducer 128. Other lumens, chambers, conduits and channels may be devoted to an optical cell counter device, for example, as shown generically as device 119 in FIG. 1. Such a cell counter device (for example a cytometry or similar) may operate with two fibers located in two separate lumens and/or ports to measure the number of and viability of cells delivered by the catheter. An example of fiber optics related application/technology is discussed in U.S. Pat. No. 8,096,984 B2 to Kucharczyk et al, of which is hereby incorporated by reference herein in its entirety It should be appreciated, that as discussed herein a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog), etc. It should be appreciated that the subject may be any applicable patient, for example.

An aspect of an embodiment of the present invention provides, but not limited thereto, a method and system for enhancing the MRI visualization of deep brain structures. The present inventors recognize that diagnostic procedures in stereotactic surgeries rely on the accuracy of targeting deep brain anatomic structures like the subcortical nuclei for successful interventions. The ability to visualize these small, often indistinct regions greatly improves clinical outcomes with therapeutic interventions.

An aspect of an embodiment of the present invention provides, but not limited thereto, a method and system that provides a catheter (such as a micro catheter) that may be stereotactically inserted in the brain of the subject (or other region) so that an infusate can be delivered, such as with convection-enhanced delivery (CED). The infusate changes the MR imaging characteristics of the tissues (e.g., of the brain) so that they can be more easily visualized for treatment. For example, in operation a diagnostic agent may be delivered for the purpose of increasing the precision with which critical structures within the brain can be targeted for subsequent delivery of therapies.

It should be appreciated that an aspect of an embodiment of the present invention provides, but not limited thereto, a method and system that can be utilized for in vivo animal laboratory experiments or for clinical procedures in humans. In an approach, pre-operative imaging may be required with MRI to initially visualize the deep brain region of interest. A computer planning workstation (and any related computer system, method and computer readable medium as required, needed or desired) is then used to, but not limited thereto, calculate the coordinates necessary for micro catheter insertion. Once the stereotactic coordinates have been obtained on the planning workstation, an incision is made in the subject (e.g., human or animal) so that a small burr hole can be drilled in the cranium at the appropriate entry site. A micro catheter may then be placed to the target with frame-based or frameless stereotactic technique (or other medical imaging systems and techniques), and then it is anchored in position for the diagnostic agent infusion. Convective properties are then used to deliver a diagnostic agent infusate to the targeted region. Serial MR imaging may be provided to monitor the diagnostic infusion until the targeted structure has been visualized. At this point, the micro catheter can be removed and the therapeutic intervention of choice can be performed. It should be appreciated that the diagnostic agent may be delivered for the purpose of increasing the precision with which critical structures within the brain can be targeted for the subsequent delivery of therapies. Further, in addition to visualizing the target structures of the brain, it should be appreciated that the diagnostic agent may also help to aid in visualizing the catheter device or other devices or systems that may disposed or advancing in and through the brain.

It should be appreciated that various computer systems, methods and computer readable media as required, needed or desired may be implemented and practiced according to any of the demands, techniques, or objectives of the various embodiments of the present invention disclosed herein.

It should be appreciated that the infusate may be a variety of materials or fluids, such as aqueous fluid, which may include the following (but are presented herein for illustration only and should not be construed as limiting the invention in any way): Saline, artificial cerebrospinal fluid (CSF), autologous CSF, lactated ringers, Dextran, Gadolinium diethylenetriamine penta-acetic acid (DTPA), Gadolinium-albumin, Phosphate Buffered Saline, and Albumin.

An aspect of an embodiment of the present invention provides, but not limited thereto, a catheter system for delivering a diagnostic agent to a site in the brain of a subject for imaging at least a portion of the brain site on a medical imaging system. The catheter system may include a catheter device having at least a first lumen, whereby first lumen may have a first lumen proximal region, a first lumen distal regional, and a first lumen longitudinal region there between. Additionally, the first lumen may be configured to convey the diagnostic agent (infusate) within the first lumen, and at least a portion of said first lumen having one or more ports configured to allow the conveyed diagnostic agent to exit from said first lumen to at least a portion of the brain site. Further yet, a portion of the catheter device may having a cross-sectional area greater than portions of catheter located proximally so as to define a seal within at least a portion of the brain site. The seal is configured to prevent or mitigate the exited diagnostic agent (infusate) from travelling proximally beyond the seal while at least a portion of the brain site can be visualized on a medical imaging system.

The diagnostic agent (infusate) changes the MR imaging characteristics of the tissues so that they can be more easily visualized for treatment. For example, in operation a diagnostic agent (infusate) may be delivered for the purpose of increasing the precision with which critical structures within the brain can be targeted for subsequent delivery of therapies.

Figure 2A:
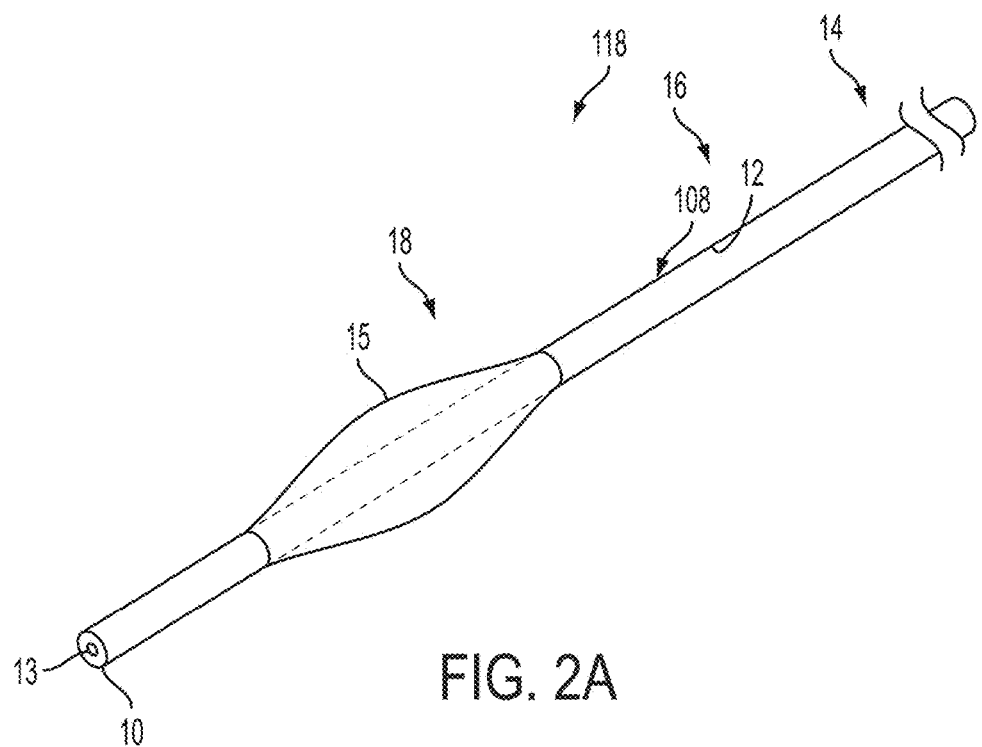
FIG. 2 provides a schematic perspective view of various embodiments of the catheter system.

FIG. 2 depicts various embodiments of the catheter system and catheter device depicted in FIG. 1. FIG. 2A depicts an aspect of an embodiment of the present invention that may be part of a catheter system 118 for delivering a diagnostic agent (not shown) or other medium to a site in the brain of a subject (or other anatomy of interest) for imaging at least a portion of the brain site (as shown in FIG. 1, for example) on a medical imaging system. The catheter system may include a catheter device 108 having at least a first lumen 12, whereby first lumen 12 may have a first lumen proximal region 14, a first lumen distal region 18, and a first lumen longitudinal region 16 there between. Additionally, the first lumen 12 may be configured to convey the diagnostic agent (infusate) within the first lumen 12, and at least a portion of the first lumen 12 having one or more ports configured to allow the conveyed diagnostic agent to exit from the first lumen 12 to at least a portion of the brain site. For instance, in the current depiction a distal port 13 is provided at the end of the distal region 18 (such as at the first lumen distal tip 10 of the catheter 108). Further yet, a portion of the catheter device 108 may have a cross-sectional area greater than portions of catheter located proximally so as to define a seal within at least a portion of the brain site. The seal is configured to prevent or mitigate the exited diagnostic agent (infusate) from travelling proximally beyond the seal while at least a portion of the brain site can be visualized on a medical imaging system. For instance, in the current depiction, an expandable component 15 may be in communication with the catheter device 108 either directly or indirectly. As depicted, the expandable component 15 may be located adjacent to the first lumen distal tip 10 of the catheter device 108 (set back in the proximal direction), while located axially within at least a portion of the first distal lumen region 18. The actual location may vary as desired, needed, or required according to the requisite operation of the device and the anatomical configurations. The expandable component 15 may be a balloon or inflatable compartment or may be activated by a balloon device, other inflatable compartment or other expandable structure or system. The expandable component 15 may have a pre-formed shape upon activation, such as expansion or inflation. It should be appreciated that the expandable component 15 is shown in an inflated or expanded position as illustrated (i.e., deployed position or state). The diagnostic agent (infusate) changes the imaging characteristics (such as for example, MR imaging characteristics) of the tissues so that they can be more easily visualized for treatment. For example, in operation a diagnostic agent (infusate) may be delivered for the purpose of increasing the precision with which critical structures within the brain can be targeted for subsequent delivery of therapies. Further, in addition to visualizing the target structures of the brain, it should be appreciated that the diagnostic agent may also help to aid in visualizing the catheter device or other devices or systems that may disposed or advanced in and through the brain (or anatomy of interest). Moreover, other materials, devices or systems may be contained in or travel through others lumens (not shown) of the catheter device or by some other related means, such as outside the catheter. In operation, images (e.g., serial MR images or other available image acquisition techniques) may monitor the diagnostic infusion until the targeted structure has been visualized. At this point, diagnostic agent may be vacated and the therapeutic intervention of choice can be performed by advancing a therapeutic agent (or other material or device) through the first lumen 12, or other alternative channels (not shown). Alternatively, a therapeutic agent may be mixed in with the diagnostic agent in the first lumen 12. Alternatively, or in addition to, an electrical lead could be passed through the first lumen 12 or alternative channels (not shown) that could be used for either recording or stimulus purposes. Still yet, alternatively, or in addition to, a stylet or other devices or systems could be passed through the first lumen 12 or alternative channels (not shown). Of course other or additional therapeutic agents or diagnostic agents (or other devices, systems, or materials) may be implemented as well as desired or required. Alternatively, the catheter device 108 (e.g., micro catheter or other size as desired, needed, or required) can be removed and the therapeutic intervention of choice can be performed by transmitting it through a new catheter or lumen, or other alternative channels (not shown).

Figure 7A:
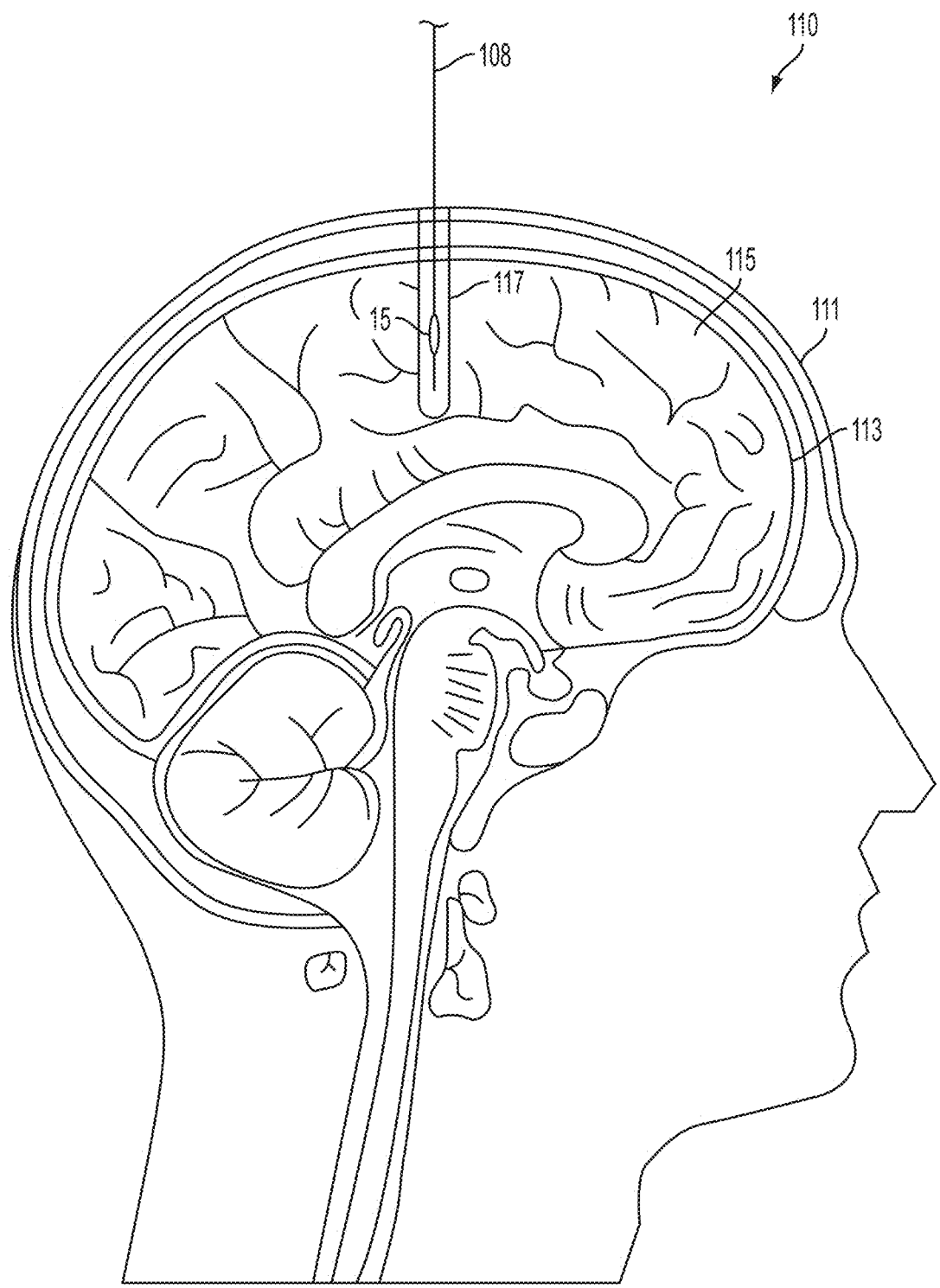
FIG. 7 provides a schematic elevations view of an embodiments of the catheter system maneuvered in an intracranial position.
Figure 7B:
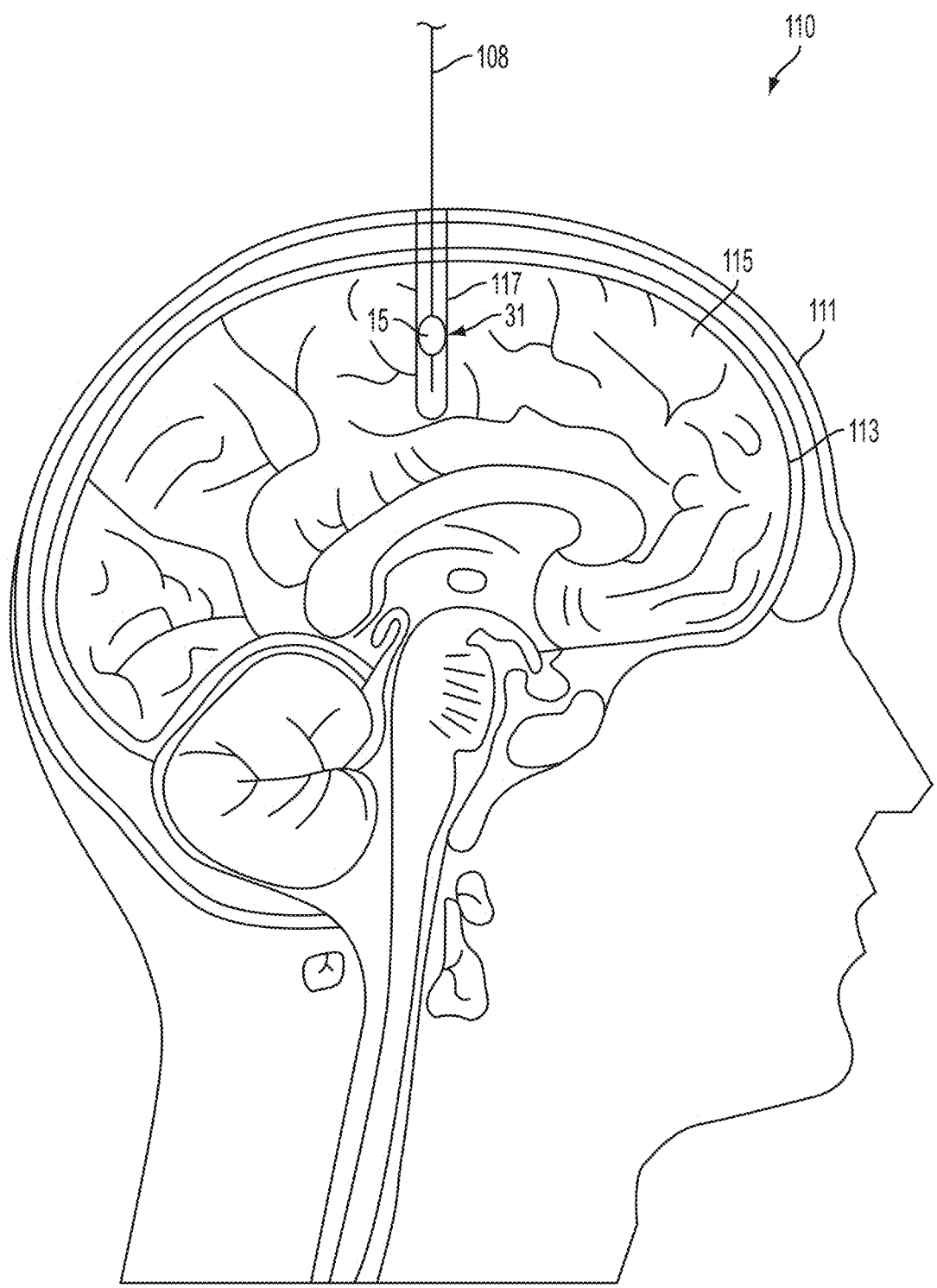

FIG. 7 provides a schematic of an embodiment of the catheter device illustrating an exemplary method of using the device. FIG. 7 depicts the catheter device 108 that is inserted forming an insertion channel 117 in the brain 113 of a subject 110, for example the parenchyma region 115. FIG. 7A depicts the expandable compartment 15 in the non-deployed position or state (i.e., non-inflated or non-expanded). Typically, boring or other cutting techniques are applied to the skull 111 in order to allow the catheter device 108 to initially gain access to the brain 113 at the outset. Whereas, FIG. 7B depicts the expandable compartment 15 in a deployed position or state (i.e., inflated or expanded). The deployed expandable compartment 15 provides a seal 31 between the catheter device 108 (or at least related portions thereof) and the insertion channel 117 so as to prevent or mitigate the exited diagnostic agent (infusate) from travelling proximally beyond the seal back up the insertion channel 117 while at least a portion of the brain site can be visualized on a medical imaging system.

Figure 2B:
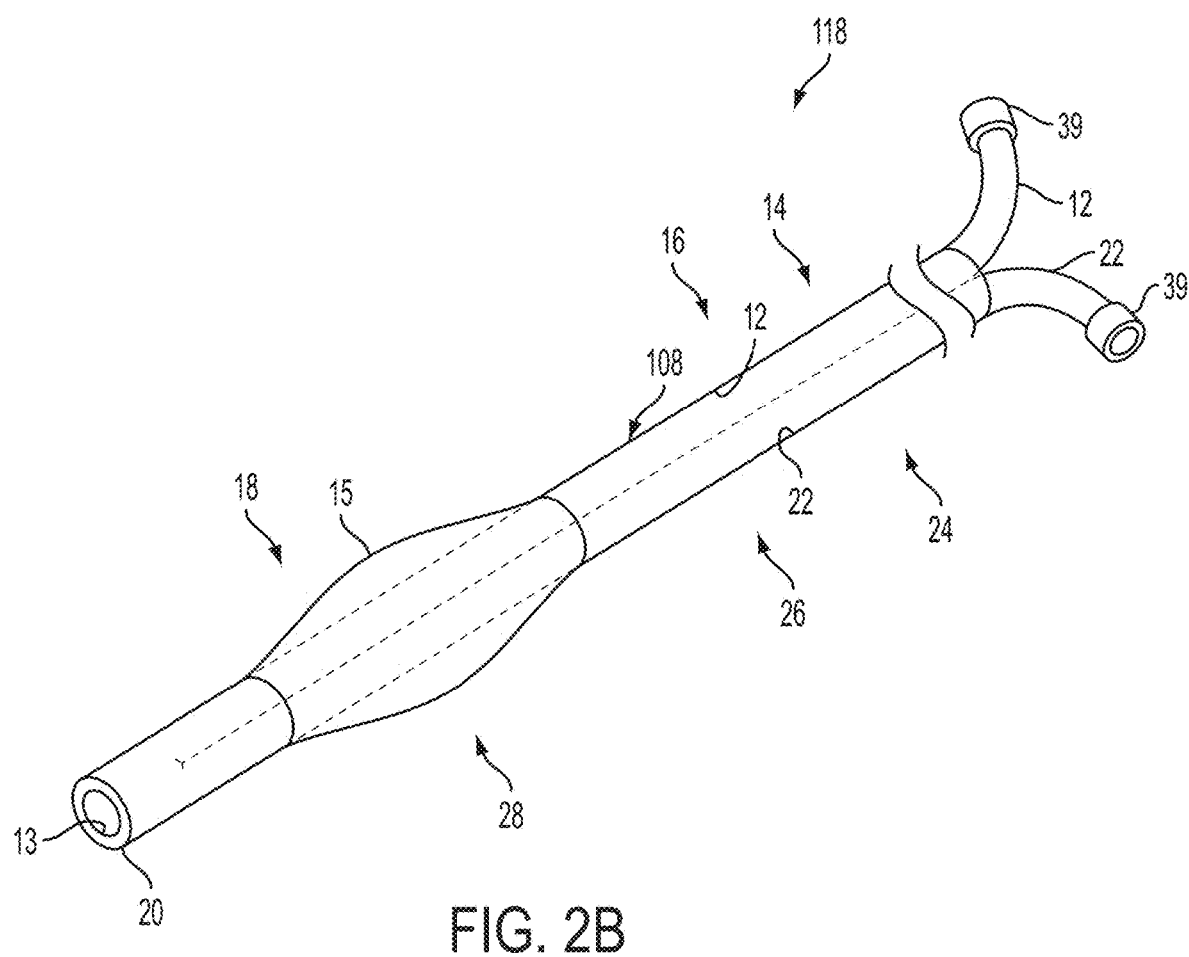

FIG. 2B depicts an aspect of an embodiment of the present invention that may provide a catheter system 118 for delivering a diagnostic agent (not shown) or other medium to a site in the brain of a subject (or other anatomy of interest) for imaging at least a portion of the brain site (as shown in FIG. 1, for example) on a medical imaging system. The catheter system 118 may include a catheter device 108 having at least a first lumen 12, whereby first lumen 12 may have a first lumen proximal region 14, a first lumen distal region 18, and a first lumen longitudinal region 16 there between. The first lumen 12 may be connected to a tubing 39 or other structure or system as desired, needed or required. The catheter device 108 may also include at least a second lumen 22, whereby second lumen 22 may have a second lumen proximal region 24, a second lumen distal regional 28, and a second lumen longitudinal region 26 there between. The second lumen 22 may be connected to a tubing 39 or other structure or system as desired, needed or required. Additionally, the first lumen 12 may be configured to convey the diagnostic agent (infusate) within the first lumen 12, and at least a portion of the first lumen 12 having one or more ports configured to allow the conveyed diagnostic agent to exit from the first lumen 12 to at least a portion of the brain site. For instance, in the current depiction a distal port 13 is provided at the end of the distal region 18 (such as at the merged first and second lumen distal tip 20 of the catheter device 108). In the current depiction, the second lumen 22 may merge or communicate with the first lumen 12, so as to share the distal port 13 in common. Thus, the second lumen 22 may be configured to convey a therapeutic agent (infusate) or other material within the second lumen 22, and therefore the second lumen 22 may be configured to merge with distal port 13 so as to allow the conveyed therapeutic agent or other material to exit from the second lumen 22 to at least a portion of the brain site. Further yet, a portion of the catheter device 108 may have a cross-sectional area greater than portions of catheter located proximally so as to define a seal within at least a portion of the brain site. The seal is configured to prevent or mitigate the exited diagnostic agent (infusate) from travelling proximally beyond the seal while at least a portion of the brain site can be visualized on a medical imaging system. For instance, in the current depiction, an expandable component 15 may be in communication with the catheter device 108 either directly or indirectly. As depicted, the expandable component 15 may be adjacent to the merged first and second lumen distal tip 20 of the catheter device 108 (set back in the proximal direction), while located axially within at least a portion of the first and second distal lumen regions 18, 28. The actual location may vary as desired, needed, or required according to the requisite operation of the device (or anatomy of interest). The expandable component 15 may be a balloon or inflatable compartment or may be activated by a balloon device, other inflatable compartment or other expandable structure or system. The expandable component 15 may have a pre-formed shape upon activation, such as expansion or inflation. It should be appreciated that the expandable component 15 is shown in an inflated or expanded position or state as illustrated (i.e., deployed position or state). The diagnostic agent (infusate) changes the imaging characteristics (such as for example, MR imaging characteristics) of the tissues so that they can be more easily visualized for treatment. For example, in operation a diagnostic agent (infusate) may be delivered for the purpose of increasing the precision with which critical structures within the brain can be targeted for subsequent or concurrent delivery of therapies. Further, in addition to visualizing the target structures of the brain, it should be appreciated that the diagnostic agent may also help to aid in visualizing the catheter device or other devices or systems that may be disposed or advanced in and through the brain (or anatomy of interest). Moreover, other materials, devices or systems may contained in or travel through others lumens (not shown) of the catheter device or by some other related means, such as outside the catheter. In operation, images (e.g., serial MR images or other available image acquisition techniques) may monitor the diagnostic infusion until the targeted structure has been visualized. At this point, a therapeutic intervention of choice can be performed by advancing a therapeutic agent (or other material or device) through the second lumen 22, or other alternative channels (not shown). Alternatively, or in addition to, a therapeutic agent may be mixed in with the diagnostic agent in the first lumen 12. Alternatively, or in addition to, an electrical lead could be passed through the first lumen 12, and/or second lumen 22, or alternative channels (not shown) that could be used for either recording or stimulus purposes. Alternatively, or in addition to, another therapeutic agent, diagnostic, or other material may be mixed in with the therapeutic agent in the second lumen 22. Still yet, alternatively, or in addition to, a stylet or other devices or systems could be passed through the first lumen 12, and/or second lumen 22; or alternative channels (not shown). Of course other or additional therapeutic agents or diagnostic agents (or other devices, systems, or materials) may be implemented as well as desired or required. Alternatively, the catheter device 108 (e.g., micro catheter or other size as desired, needed or required) can be removed and the therapeutic and diagnostic intervention of choice can be performed by advancing the materials through a new catheter or lumen, or other alternative channels (not shown).

It should be appreciated that the expandable component(s) 15 discussed herein may can take on all shapes along the entire continual geometric spectrum of manipulation of x, y and z planes of the catheter device or lumen(s) to create, for example but not limited thereto, a relatively conical, olive, ellipsoid, hemispherical, tubular, ring, cylindrical, multifaceted or spherical shape with changing of the axial direction as well as traverse to the axis. The size of the expandable components could also be manipulated by varying the compliance of the material and inflation pressure. The compliance and pressure may allow for the expandable components to conform to the catheter device, anatomy, or other devices or structures.

It should be appreciated that expandable components 15 discussed herein may be single compartment or multiple compartments or other types of expansion type of structure. A component may have a pre-formed shape and/or have a size or shape being able to be controlled by the operator. The size of the expandable component could be a function of material compliance and inflation pressure, or physical structure.

It should be appreciated that any of the elements, parts, or components of the catheter device or catheter system may be adapted to be visible on a medical imaging system. The elements, parts, or components of the catheter device or catheter system may achieve this visibility by 1) material itself, 2) structures, systems or devices disposed thereto, 3) coatings applied thereon, or 4) any combination thereof. For example, a coating could be applied to the any of the elements, parts, or components, of the catheter device or catheter system. For example a coating may be applied to the outer wall of the catheter wall designed to enhance the MR visibility to help differentiate the catheter position with the brain tissues. For instance, the wall may be impregnated or coated with gadolinium (Gd), contrast-enhancing MR-compatible alloys and materials, radio-opague substances such as barium sulfate, bismuth, tungsten or the like. Similarly, a micro coil or the like could be dispose on any of the elements, parts, or components, of the catheter device or catheter system. For example, a RF coil may be coupled to the MR system to image the catheter. The RF could be connected or integrated into the structure of the catheter device or system.

An example of a coil device may be a radio frequency (RF) microcoil that may be wound circumferentially of any of the lumens or catheter device, or any related components. The physical and electrical characteristics of the RF microcoil elements are such as to enhance the contrast of magnetic resonance images made of body parts into which the catheter means incorporating the microcoil elements are inserted. Active MR visualization of drug, cell, and gene vector delivery can be achieved by means of one or more RF microcoils positioned on the catheter as disclosed in U.S. Pat. No. 6,026,316 to Kucharczyk et al.; of which is hereby incorporated by reference herein in its entirety (and which is not admitted to be prior art with respect to the present invention by inclusion in this section). Single microcoils may be used separately or the combination of microcoils may be constructed in an array that may be used together to optimally image the surrounding environment, including the tissue structure and function within the field of response of the microcoils. The system of microcoils may, by way of non-limiting example, be used for very small (picoliter, nanoliter or microliter) injections measured within a solenoid volume RF microcoil, which by design is mainly sensitive to the volume inside the coil. The imaging volume in such a use is usually directly related to the diameter of the RF coil.

Additionally, it should be appreciated that the catheter device or lumens may be comprised of a variety structures including, but not limited thereto, the following: constituting various types of conduits, channels, passages, pipes, tunnels, and/or bounded tubular surfaces or the like. Moreover, the tubes, catheter, lumens, may have a variety of cross-sectional shapes including, but not limited to the following geometric shapes: circular, oval, multi-faceted, square, rectangular, hexagonal, octagons, parallelogram hexagonal, triangular, ellipsoidal, pentagonal, octagonal, or combinations thereof or other desired shapes, including variable diameter or cross-section geometries and irregular geometries.

Further, it should be appreciated that any of the apertures (e.g., port holes or the like) discussed herein may have a variety of shapes such as, but not limited thereto, the following circular, oval, multi-faceted, square, rectangular, hexagonal, octagons, parallelogram hexagonal, triangular, ellipsoidal, pentagonal, octagonal, or combinations thereof or other desired shapes.

Similarly, the apertures (port holes or the like) discussed herein may be of a variety structures such as, but not limited thereto, the following: recess, port, duct, trough, bore, inlet, hole, perforation, channel, passage, slot, dialysis-like membrane, semi-permeable membrane, orifice or the like.

Moreover, it should be appreciated that the various components of the catheter device or lumens, as well as elements, parts, or components, of the catheter system may be a variety of commercially available materials used for all types of catheter systems. Some examples of materials used for the inner and outer catheters may include, but not limited thereto, the following: polymers, rubber, plastic, composites, metals, ceramics, hydrogels, dialysis membranes and other membranous materials, MR-compatible alloys and materials, and other organic and inorganic compounds and substances and the like.

Still yet, it should be appreciated that the various components of the catheter device or lumens, as well as elements, parts, or components, of the catheter system may be flexible or rigid or combination thereof as required or desired for intended use.

Similarly, it should be appreciated that the various components of the catheter device or lumens, as well as elements, parts, or components, of the catheter system may be may provide volume contoured delivery/withdrawal (i.e., transfer) of a medium by adjusting its geometry and flexibility/rigidity according to the target location or anatomy (or region, including structure and morphology of any lesion) being treated or imaged.

It should be appreciated that various sizes, dimensions, contours, rigidity, shapes, flexibility and materials of any of the components or portions of components in the various embodiments discussed throughout may be varied and utilized as desired or required. Similarly, locations and alignments of the various components may vary as desired or required.

It should be appreciated that any of the components or modules referred to with regards to any of the present invention embodiments discussed herein, may be integrally or separately formed with one another. Further, redundant functions or structures of the components or modules may be implemented.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that any of the medium discussed herein may regarding transference of the medium may comprises at least one of the following: chemotherapies, cell slurries, gene therapy vectors, growth factors, contrast agents, angiogenesis factors, radionuclide slurries, anti-infection agents, anti-tumor compounds, receptor-bound agents and/or other types of drugs, therapeutic and/or diagnostic or agents, aqueous solution, saline, artificial cerebrospinal fluid (CSF), autologous CSF, lactated ringers, Dextran, Gadolinium diethylenetriamine penta-acetic acid (DTPA), Gadolinium-albumin, Phosphate Buffered Saline, and Albumin, or any pharmaceutical accepted carrier.

It should be appreciated, for example but not limited thereto, that the characteristics of the catheter device such as the ports, seals, and lumens, provides the ability to 1) facilitate consistency and eliminate imaging artifact and 2) optimize the infusate for safe and optimal MRI visualization.

Figure 2C:
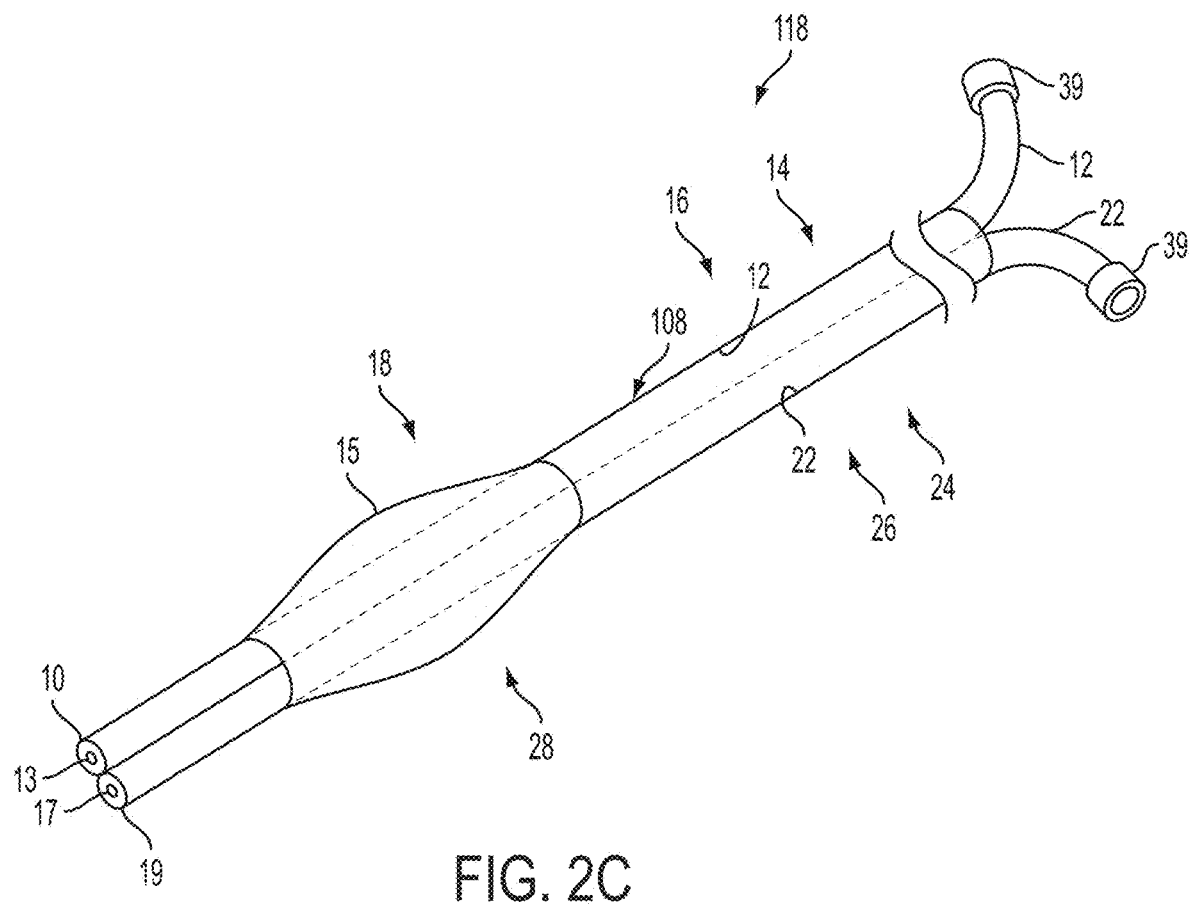

FIG. 2C depicts an aspect of an embodiment of the present invention that may provide a catheter system 118 for delivering a diagnostic agent (not shown) or other medium to a site in the brain of a subject (or other anatomy of interest) for imaging at least a portion of the brain site (as shown in FIG. 1, for example) on a medical imaging system. The catheter device 108 depicted in FIG. 2C is similar to the catheter device 108 depicted in the FIG. 2B except for the fact, for example, that the first lumen 12 and second lumen 22 do not necessarily merge or communicate with one another thereby resulting in each of the first and second lumens 12, 22 having separate and distinct distal ports 13, 17 (e.g., first and second distal ports) at respective first and second lumen distal tips 10, 19.

Figure 3A:
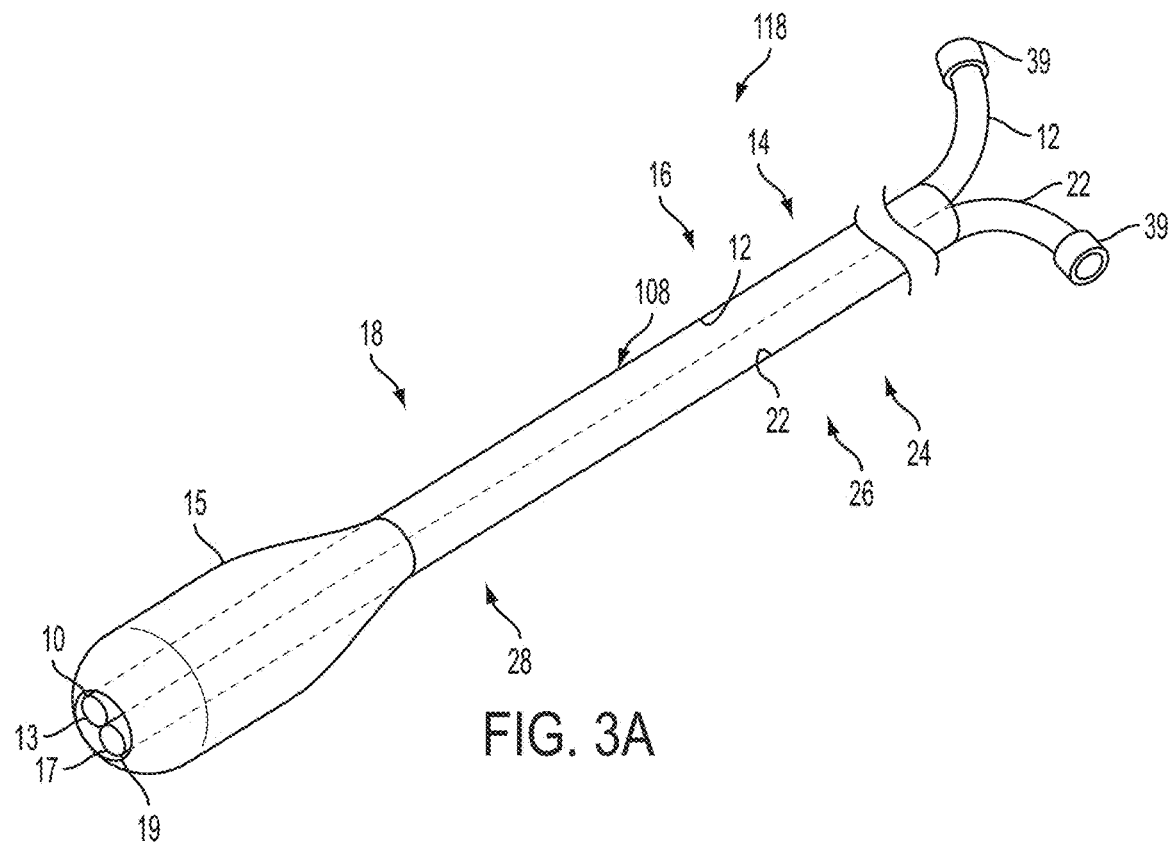
FIG. 3 provides a schematic perspective view of various embodiments of the catheter system.

FIG. 3A depicts an aspect of an embodiment of the present invention that may provide a catheter system 118 for delivering a diagnostic agent (not shown) or other medium to a site in the brain of a subject (or other anatomy of interest) for imaging at least a portion of the brain site (as shown in FIG. 1, for example) on a medical imaging system. The catheter device 108 depicted in FIG. 3A is similar to the catheter device 108 depicted in the FIG. 2C except for the fact, for example, the expandable component 15 is located beginning generally at the first and second lumen distal tips 10, 19 and generally spanning axially at least in part at the first and second distal lumen regions 18, 28 of the catheter device 108. The actual location may vary as desired, needed, or required according to the requisite operation of the device or anatomy of interest.

Figure 3B:
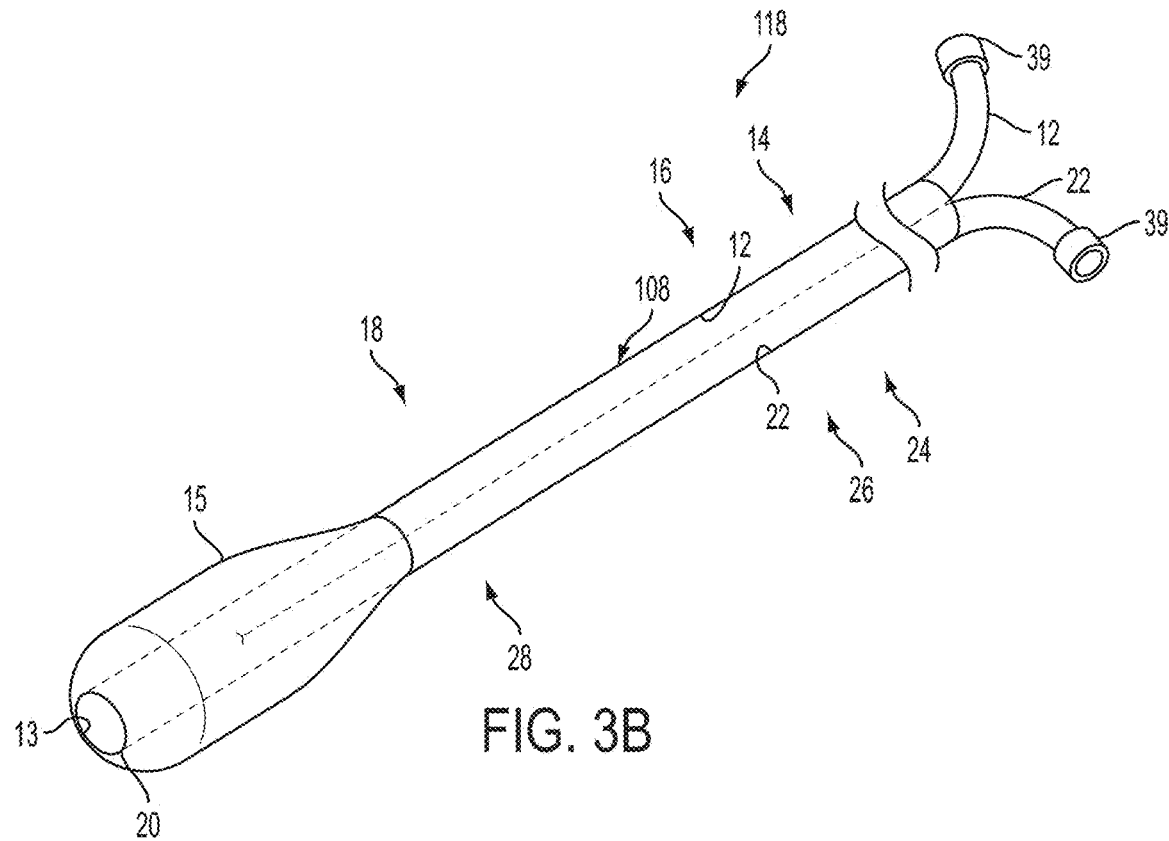

FIG. 3B depicts an aspect of an embodiment of the present invention that may provide a catheter system 118 for delivering a diagnostic agent (not shown) or other medium to a site in the brain of a subject (or other anatomy of interest) for imaging at least a portion of the brain site (as shown in FIG. 1, for example) on a medical imaging system. The catheter device 108 depicted in FIG. 3B is similar to the catheter device 108 depicted in the FIG. 2B except for the fact, for example, the expandable component 15 is located beginning generally at the merged first and second lumen distal port 20 and generally spanning axially at least in part at the first and second distal lumen regions 18, 28 of the catheter device 108. The actual location may vary as desired, needed, or required according to the requisite operation of the device or anatomy of interest.

Figure 4A:
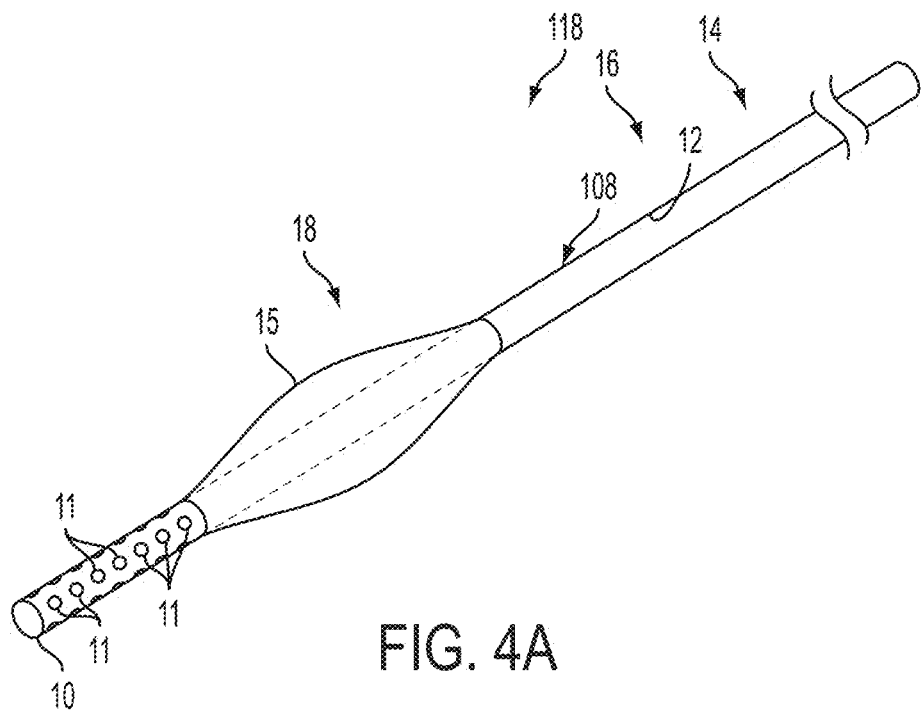
FIG. 4 provides a schematic perspective view of various embodiments of the catheter system.
Figure 4B:
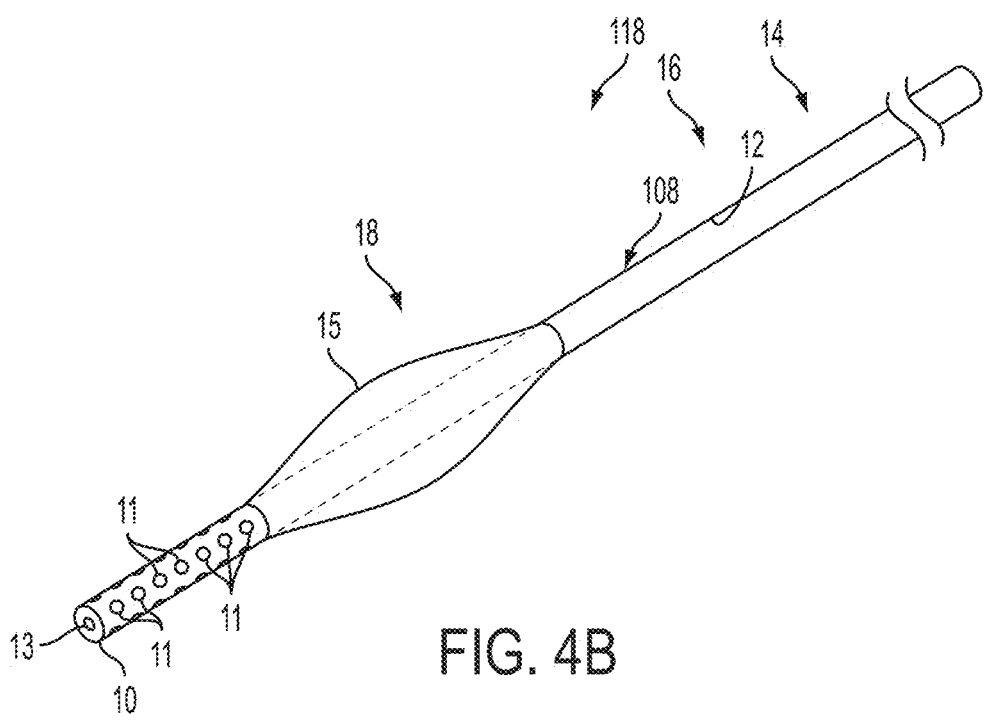

FIG. 4B depicts an aspect of an embodiment of the present invention that may be part of a catheter system 118 for delivering a diagnostic agent (not shown) or other medium to a site in the brain of a subject (or other anatomy of interest) for imaging at least a portion of the brain site (as shown in FIG. 1, for example) on a medical imaging system. The catheter device 108 depicted in FIG. 4B is similar to the catheter device 108 depicted in the FIG. 2A except for the fact, for example, that in addition to the first lumen distal port 13 it also includes a plurality or array of side ports 11. The plurality or array of side ports 11 may be located at least in part axially distal from at least a portion of the expandable component 15. As depicted, the plurality or array of side ports 11 are located beginning at the first lumen distal tip 10 and generally spanning axially at least in part of the second distal lumen region 18, 28 of the catheter device 108. As depicted the plurality or array of side ports 11 extend to the expandable component 15, but it should be appreciated that they do not necessarily need to extend completely to the expandable component 15. The array or plurality of ports 11 provide, among other things, the ability to insure uniform spread of solution, medium, or infusate while exiting from the array or plurality of ports 11. It should be appreciated that at least a portion of the expandable compartment 15 should be located axially proximal relative to the side ports 11 so as to accommodate the formation of the seal between the catheter device 108 and a portion of the brain site, and while preventing or mitigation backflow from occurring.

FIG. 4A depicts an aspect of an embodiment of the present invention that may be part of a catheter system 118 for delivering a diagnostic agent (not shown) or other medium to a site in the brain of a subject (or other anatomy of interest) for imaging at least a portion of the brain site (as shown in FIG. 1, for example) on a medical imaging system. The catheter device 108 depicted in FIG. 4A is similar to the catheter device 108 depicted in the FIG. 4B except for the fact, for example, the catheter device 108 exists without a first lumen distal port.

Figure 4C:
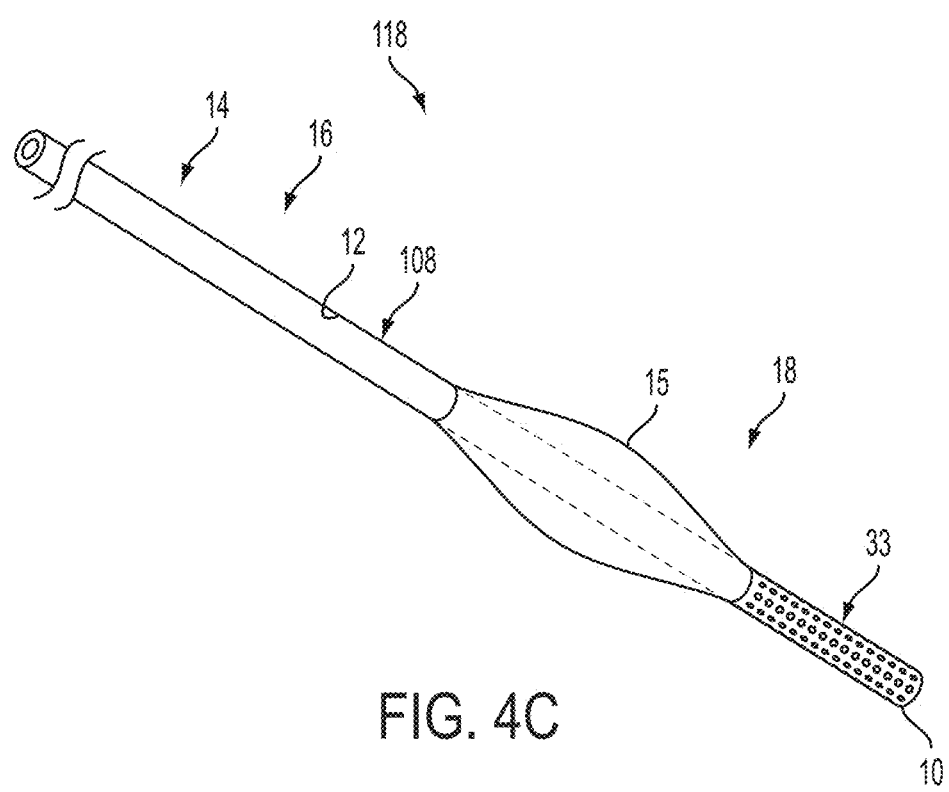

FIG. 4C depicts an aspect of an embodiment of the present invention that may be part of a catheter system 118 for delivering a diagnostic agent (not shown) or other medium to a site in the brain of a subject (or other anatomy of interest) for imaging at least a portion of the brain site (as shown in FIG. 1, for example) on a medical imaging system. The catheter device 108 depicted in FIG. 4C may be similar to the catheter device 108 depicted in the FIG. 4A in the aspect that, for example, the catheter device 108 exists without a first lumen distal port. Alternatively, the catheter device 108 depicted in FIG. 4C may be similar to the catheter device 108 depicted in the FIG. 4B in the aspect that, for example, the catheter device 108 may have a first lumen distal port 13. However, the catheter device 108 depicted in FIG. 4C may be similar to the catheter device 108 depicted in the FIGS. 4A and 4B except for the fact, for example, that instead of having a plurality or array of side ports it has dialysis-like membrane structure or membrane.

Figure 5A:
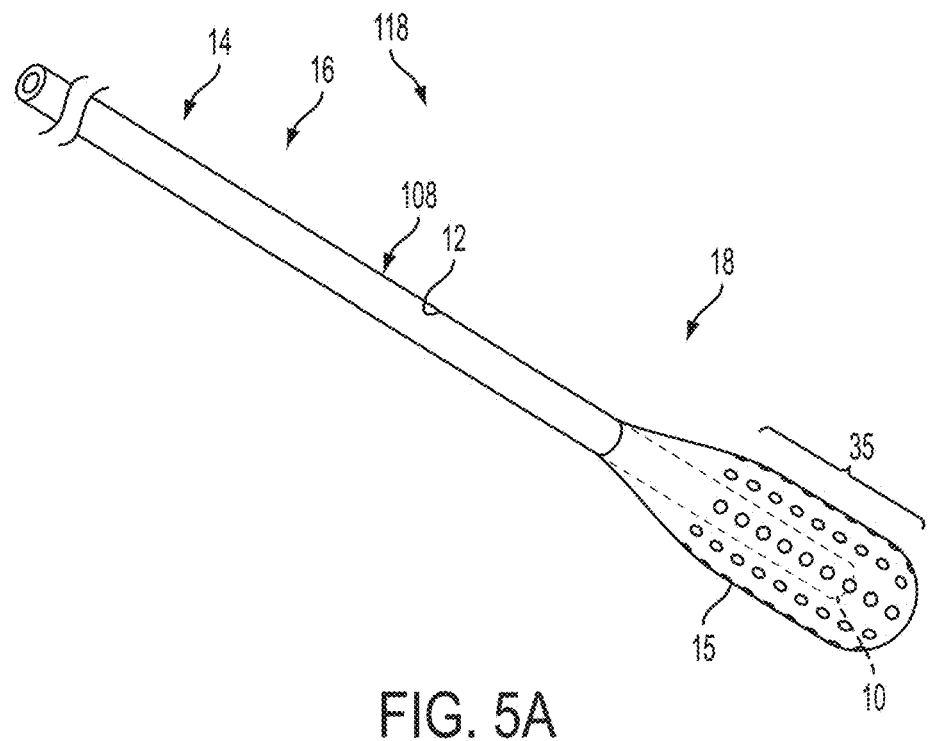
FIG. 5 provides a schematic perspective view of various embodiments of the catheter system.
Figure 5B:
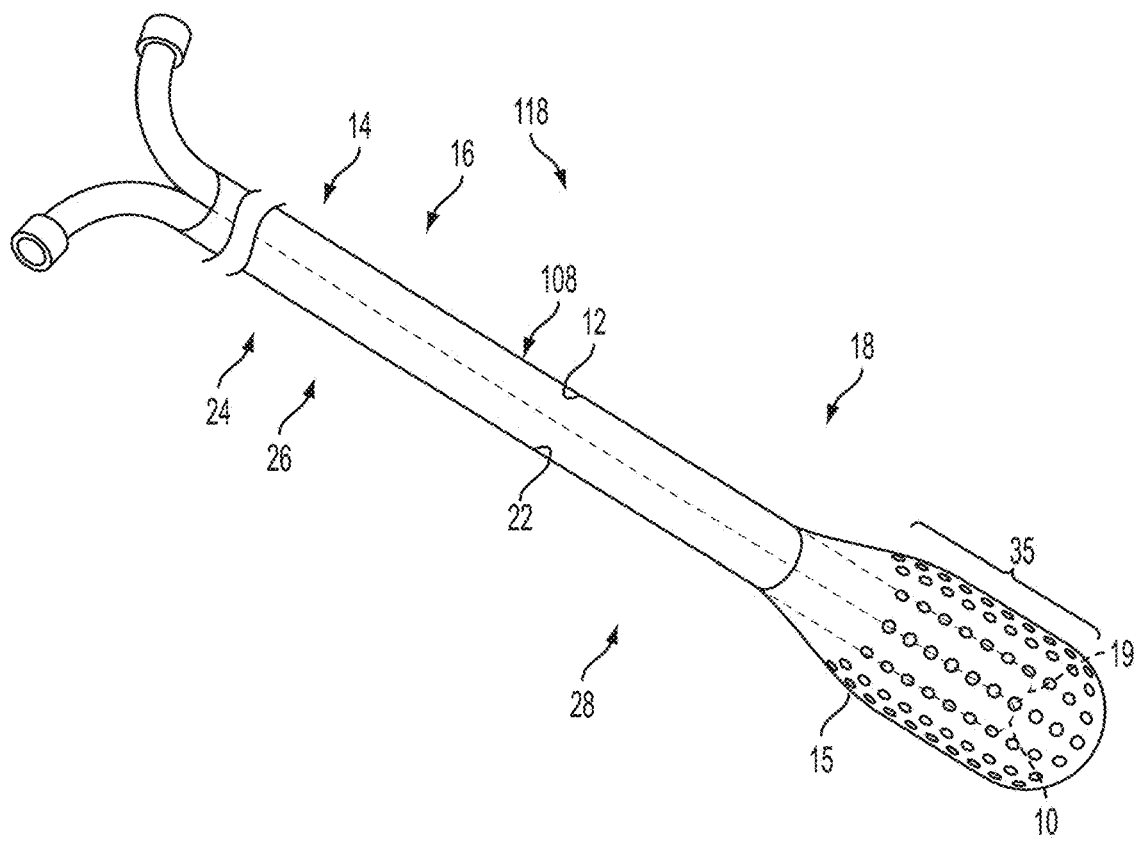
Figure 6A:
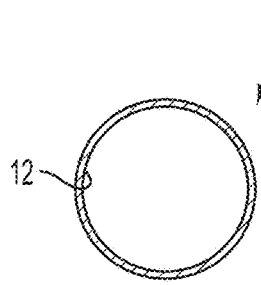
FIG. 6 provides a schematic exemplary cross-sectional view of various embodiments of the catheter device.
Figure 6B:
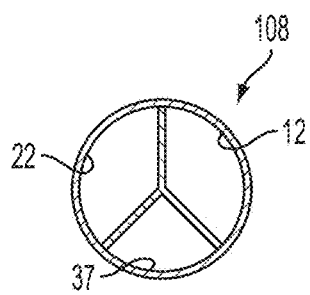
Figure 6C:
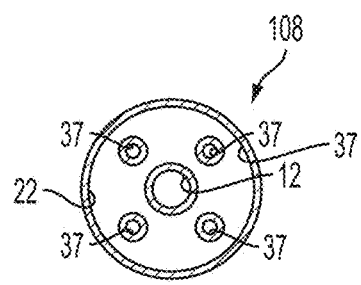
Figure 6D:
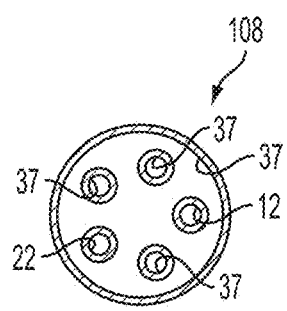
Figure 6E:
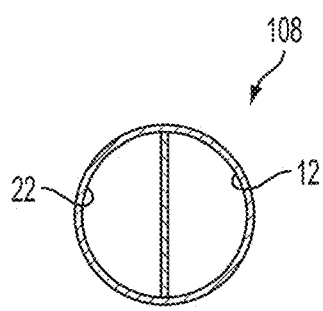
Figure 6F:
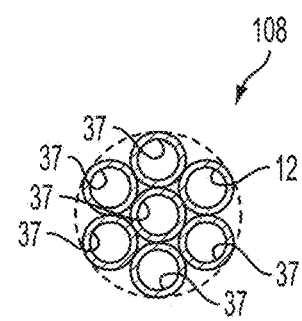
Figure 6G:
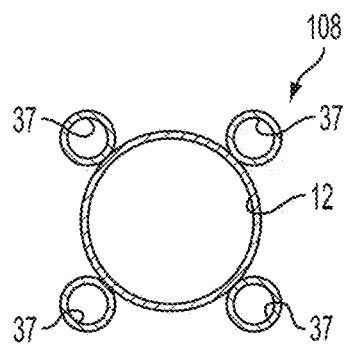
Figure 6H:
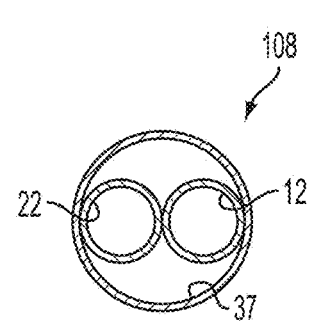
Figure 6I:
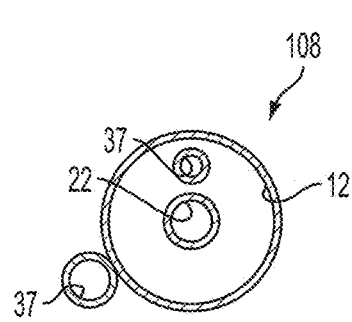
Figure 6J:
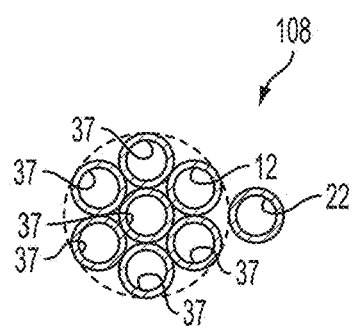

FIG. 5B depicts an aspect of an embodiment of the present invention that may be part of a catheter system 118 for delivering a diagnostic agent (not shown) or other medium to a site in the brain of a subject (or other anatomy of interest) for imaging at least a portion of the brain site (as shown in FIG. 1, for example) on a medical imaging system.

The catheter device 108 depicted in FIG. 5B is similar to the catheter device 108 depicted in the FIG. 3B except for the fact, for example, that in place having a merged first and second lumen distal port 20 that instead there exists expandable component ports 35. Although not shown, it should be appreciated that the catheter device could have both the merged/common first and second lumen distal port 20 as well as the expandable component portholes 35. It should be also appreciated that although not shown, the catheter device could have separate and distinct first and second lumens (or more) as well as the expandable component portholes 35.

FIG. 5A depicts an aspect of an embodiment of the present invention that may be part of a catheter system 118 for delivering a diagnostic agent (not shown) or other medium to a site in the brain of a subject (or other anatomy of interest) for imaging at least a portion of the brain site (as shown in FIG. 1, for example) on a medical imaging system. The catheter device 108 depicted in FIG. 5A is similar to the catheter device 108 depicted in the FIG. 5B except for the fact, for example, that the catheter device 108 has only a first lumen 12 rather than both first and second lumen.

FIG. 6 depicts an aspect of various embodiments of the present invention that may provide a catheter system for delivering a diagnostic agent (not shown) or other medium to a site in the brain of a subject (or other anatomy of interest) for imaging at least a portion of the brain site (as shown in FIG. 1, for example) on a medical imaging system. FIGS. 6A-6J provide a schematic view of a representative cross-section of a catheter device 108 that may be taken at its distal lumen region, for example. As illustrated the catheter device may include a first lumen 12, second lumen 22, and a variety of ancillary lumens 37. The lumens may be any channel, passage, chamber, or conduit to transfer the requisite medium(s). FIGS. 6F and 6J depict lumens that are not necessarily contained in an enclosed structure per se but rather may assembled, associated or connected together to the extent necessary or desired to carry out the various techniques and systems of the present invention.

EXAMPLES

Practice of an aspect of an embodiment (or embodiments) of the invention will be still more fully understood from the following examples and experimental results, which are presented herein for illustration only and should not be construed as limiting the invention in any way.

Example and Experimental Results Set No. 1

Turning to FIG. 8, the inventors observed in a patient's brain MRI (of a human), which was taken a few weeks postoperatively, improved visualization of deep brain nuclei as a result of the edema from a low grade infection. It is believed by the inventors that additional aqueous fluid in the brain and its extracellular space around the deep brain structures enhances their MRI characteristics owing to a differential absorption in grey and white matter.

Figure 8A:
FIG. 8 provides a MRI depiction of subject's brain (human) whereby an edema is present (right side) and absent in the brain (left side) of the subject.
FIG. 8B provides a partial view of FIG. 8A and which is set at a higher magnification.
Figure 8B:

FIG. 8 represents an axial T2 weighted MR image of deep brain stimulating electrodes positioned in the subthalamus. Note the edema around the electrode as shown on the right side of the brain of FIGS. 8A-B, which delineates the borders of the subthalamus, red nucleus, internal capsule, and internal segment of the globus pallidum. As a control, these anatomic structures are not evident without edema, as shown on the left side of the brain of FIGS. 8A-B. FIG. 8B provides a partial view of FIG. 8A and which is set at a higher magnification.

Example and Experimental Results Set No. 2

Figure 9A:
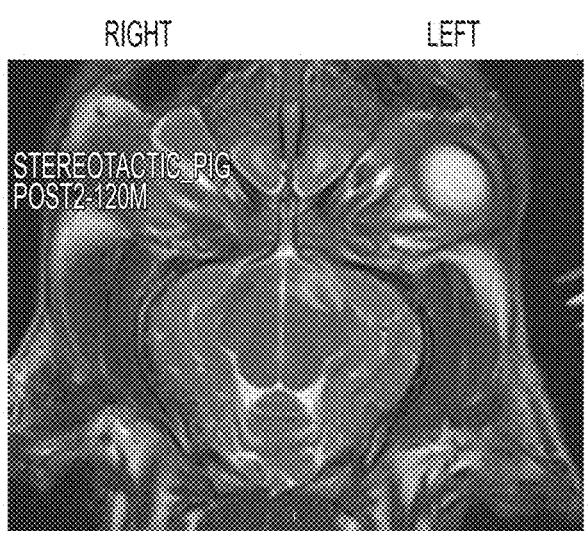
FIG. 9 provides a MRI depiction of subject's brain (swine) whereby saline is present (right side) and absent (left side) in the brain of the subject.
FIG. 9B provides a partial view of FIG. 9A and which is set at a higher magnification.
Figure 9B:
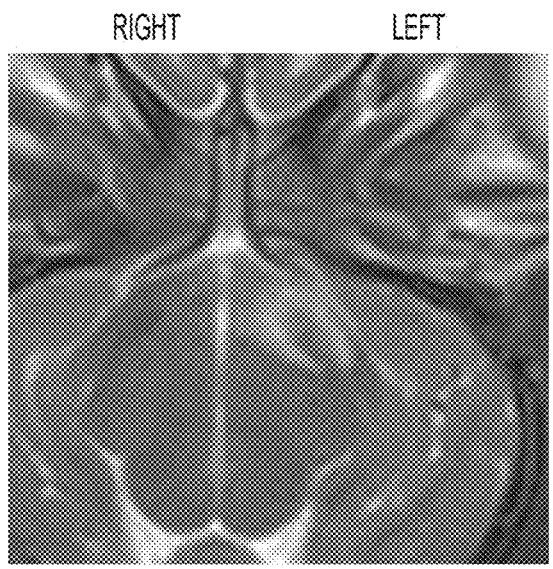

FIG. 9 represents an MR image from an in vivo experiment where saline was convected to the swine basal ganglia. Note the enhanced anatomical boundaries of the globus pallidum as shown on the right side of the brain in FIGS. 9A-9B, as compared to the contralateral side (i.e., left side of the brain) which was not infused as shown in FIGS. 9A-B. FIG. 9B provides a partial view of FIG. 9A and which is set at a higher magnification.

Example and Experimental Results Set No. 3

Using a commercially available FDA-approved infusion catheter provided by NexGen Medical Systems Inc. and a custom stereotactic frame, the present inventors convected normal saline into the basal ganglia of 25 pound swine. Infusion rates were varied between 1-5 microliters per minute and total infusion volumes were less than 500 microliters. The infusions were performed with the animal positioned in a 3 Tesla MRI, so that imaging was acquired continuously at 15 minute intervals. Six animals were infused into the right basal ganglia with the contralateral side serving as a control. Histological analysis of the brains was obtained at early and late time points in accordance with standard FDA toxicity guidelines.

Figure 10:
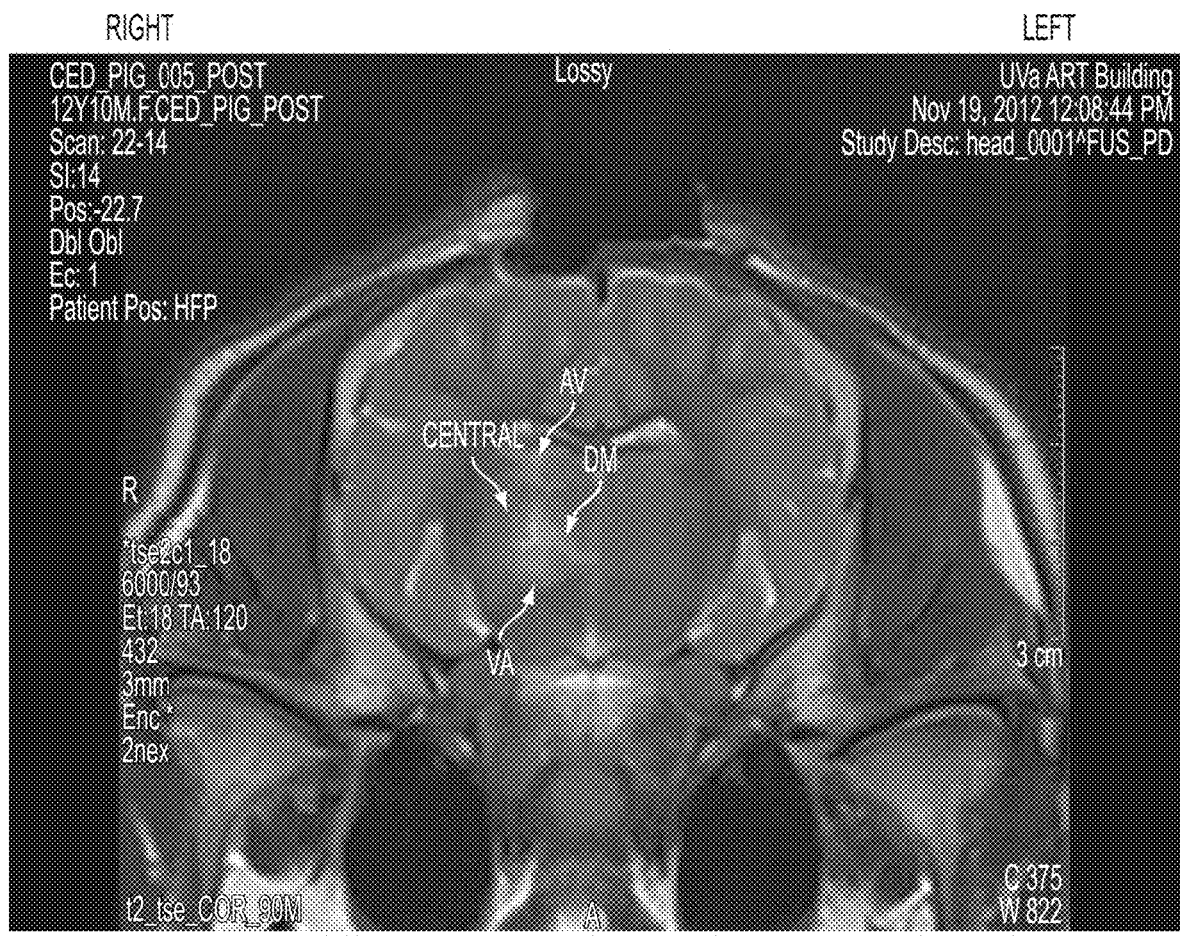
FIG. 10 provides a MRI depiction of subject's brain (swine) whereby saline is present on one side (right side) and absent on the other side (left side) of the brain of the subject.

FIG. 10 represents a Coronal T2 MRI scan performed at the end of infusion of 450 microliters of normal saline into swine. Note the differentiation of the deep nuclei not present on the left side of the brain which was not infused. Five of the six animals demonstrated similar MR imaging results with enhanced differentiation of the deep brain nuclei (e.g., on the right side of the brain). White matter tracts became identifiable from the underlying nuclei within small volumes of infusion, typically 15 microliters. Deep brain nuclei became apparent on the right side of the brain during the infusions as compared to the control, contralateral side (i.e., left side of the brain). Significant backflow of the infusate without improved MRI visualization of the target was observed in only one animal.

Example and Experimental Results Set No. 4

Figure 11A:
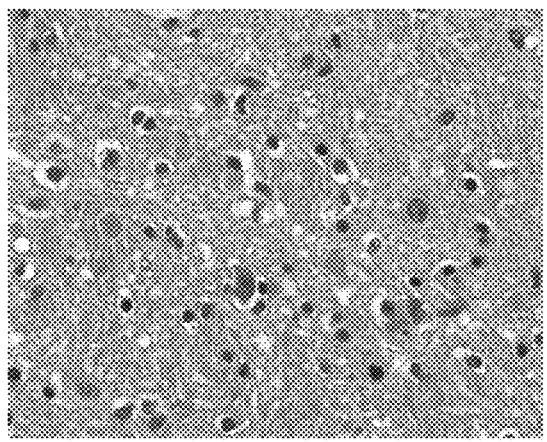
FIGS. 11A and 11B represent a histologic cross section of swine brain after infusion of 450 microliters of normal saline which demonstrated Pyknotic neurons and ballooning neurons indicating unacceptable damage to neural tissue.
Figure 11B:
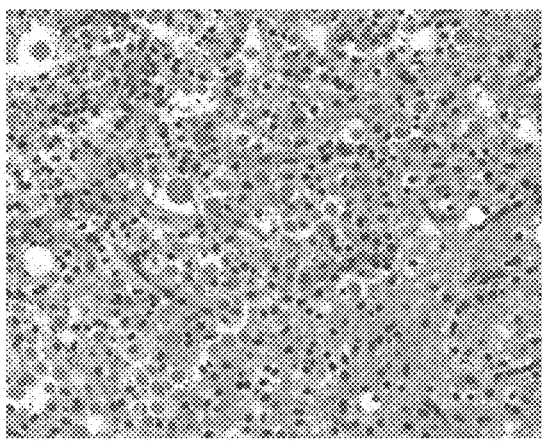

FIG. 11 represents a histologic cross section of swine brain after infusion of 450 microliters of normal saline which demonstrated pyknotic neurons and axonal swelling indicative of neuronal injury. While none of the animals exhibited clinical evidence of neurologic dysfunction, histologic analysis of brains within 1 week and after 1 month of infusion demonstrated mild, microscopic injury to neurons, which likely resulted from the osmotic gradient between the normal saline infusate which is hypertonic to the swine brain and CSF. FIG. 11B provides a partial view of FIG. 11A and which is set at a higher magnification.

Accordingly, this preliminary study confirms the concept that convection-enhanced delivery (CED) of saline leads to a differential uptake of water content in grey and white matter with enhanced MRI visualization of deep brain anatomy similar to what was observed in the patient with edema from a localized infectious process. Backflow along the catheter track in one animal led to a failed attempt highlighting the need to improve certain approaches of a microcatheter. Histological analysis revealed unexpected neuronal injury from normal saline which is hypertonic and illustrates the need to test and optimize additional infusates.

Additional Examples

Example 1. An aspect of an embodiment of the present invention provides, but not limited thereto, a catheter system for delivering a diagnostic agent to a site in the brain of a subject for imaging at least a portion of the brain site on a medical imaging system. The catheter system may comprise: a catheter device, the catheter device includes as a first lumen, the first lumen having a first lumen proximal region, a first lumen distal regional, and a first lumen longitudinal region there between; the first lumen configured to convey a diagnostic agent within the first lumen, and at least a portion of the first lumen having one or more ports configured to allow the conveyed diagnostic agent to exit from the first lumen to at least a portion of the brain site; and a portion of the catheter device having a cross-sectional area greater than portions of the catheter located proximally so as to define a seal within at least a portion of the brain site, wherein the seal is configured to prevent the exited diagnostic agent from travelling proximally beyond the seal while at least a portion of the brain site can be visualized on a medical imaging system.

Example 2. The system of example 1, further comprising: a first lumen diagnostic agent, wherein the first lumen diagnostic agent comprises: autologous cerebrospinal fluid (CSF).

Example 3. The system of example 1 (as well as subject matter of any combination of example 2), further comprising: a first lumen diagnostic agent, wherein the first lumen diagnostic agent comprises: artificial cerebrospinal fluid (CSF).

Example 4. The system of example 1 (as well as subject matter of one or more of any combination of examples 2-3), further comprising: a first lumen diagnostic agent, wherein the first lumen diagnostic agent comprises: saline.

Example 5. The system of example 1 (as well as subject matter of one or more of any combination of examples 2-4), further comprising: a first lumen diagnostic agent, wherein the first lumen diagnostic agent comprises an aqueous fluid.

Example 6. The system of example 5 (as well as subject matter of one or more of any combination of examples 2-4), wherein the aqueous fluid comprises at least one of the following: lactated ringers, Dextran, Gadolinium diethylenetriamine penta-acetic acid (DTPA), Gadolinium-albumin, Phosphate Buffered Saline, and Albumin.

Example 7. The system of example 1 (as well as subject matter of one or more of any combination of examples 2-6), wherein the catheter device comprises a first lumen distal tip, and the one or more ports is located at the distal tip of the first lumen.

Example 8. The system of example 7 (as well as subject matter of one or more of any combination of examples 2-7), wherein additional the one or more ports is located on the wall of the first lumen located at the first lumen distal region.

Example 9. The system of example 1 (as well as subject matter of one or more of any combination of examples 2-8), wherein the one or more ports is located on the wall of the first lumen located at the first lumen distal region.

Example 10. The system of example 9 (as well as subject matter of one or more of any combination of examples 2-8), wherein the one or more ports comprises a plurality or array of holes or a dialysis-like membrane.

Example 11. The system of example 1 (as well as subject matter of one or more of any combination of examples 2-10), whereby the system for delivering a second diagnostic agent, wherein the system further comprises: a second lumen, the second lumen having a second lumen proximal region, a second lumen distal regional, and a second lumen longitudinal region there between; the second lumen configured to convey a second lumen agent within the second lumen, and at least a portion of the second lumen having one or more second lumen agent ports configured to allow the conveyed second lumen agent to exit from the second lumen to at least a portion of the brain site; and wherein the seal is configured to prevent the exited second lumen agent from travelling proximally beyond the seal.

Example 12. The system of example 11 (as well as subject matter of one or more of any combination of examples 2-10), further comprising: a second lumen diagnostic agent, wherein the second lumen agent comprises: one or more therapeutic agents.

Example 13. The system of example 11 (as well as subject matter of one or more of any combination of examples 2-10 and 12), further comprising: a second lumen diagnostic agent, wherein the second lumen agent comprises: one or more diagnostic agents.

Example 14. The system of example 11 (as well as subject matter of one or more of any combination of examples 2-10 and 12-13), wherein the second lumen being configured to accommodated at least one of the following: stylet, electrical lead, ancillary catheter, solid state sensor, electrical conductor, sampling tube, abrading tip, optical fiber, deep brain simulation (DBS) device, or pH sensor.

Example 15. The system of example 11 (as well as subject matter of one or more of any combination of examples 2-10 and 12-14), wherein the second lumen device comprises at least one of the following at least partially disposed therein: stylet, electrical lead, ancillary catheter, solid state sensor, electrical conductor, sampling tube, abrading tip, optical fiber, deep brain simulation (DBS) device, or pH sensor.

Example 16. The system of example 11 (as well as subject matter of one or more of any combination of examples 2-10 and 12-15), whereby the system for conveying a third lumen material or device, wherein the system further comprises: a third lumen, the third lumen having a third lumen proximal region, a third lumen distal regional, and a third lumen longitudinal region there between; and the third lumen configured to convey a third lumen material or device.

Example 17. The system of example 11 (as well as subject matter of one or more of any combination of examples 2-10 and 12-16), wherein the brain site includes the parenchyma.

Example 18. The system of example 11 (as well as subject matter of one or more of any combination of examples 2-10 and 12-17), wherein the brain site includes within the cerebrovasculature.

Example 19. The system of example 16 (as well as subject matter of one or more of any combination of examples 2-15 and 17-18), further comprising: a third lumen device at least partially disposed therein.

Example 20. The system of example 19 (as well as subject matter of one or more of any combination of examples 2-18), wherein the third lumen device comprises at least one of the following: stylet, electrical lead, ancillary catheter, solid state sensor, electrical conductor, sampling tube, abrading tip, optical fiber, deep brain simulation (DBS) device, or pH sensor.

Example 21. The system of example 16 (as well as subject matter of one or more of any combination of examples 2-15 and 17-20), wherein the system further comprises:
a third lumen material at least partially disposed therein.

Example 22. The system of example 21 (as well as subject matter of one or more of any combination of examples 2-20), wherein the third lumen material comprises at least one of the following: one or more diagnostic agents and one or more therapeutic agents.

Example 23. The system of example 1 (as well as subject matter of one or more of any combination of examples 2-22), wherein the greater area cross-section includes at least in part an expandable component in communication with the catheter device.

Example 24. The system of example 23 (as well as subject matter of one or more of any combination of examples 2-22), wherein the expandable component is axially located at a portion of the first lumen distal region.

Example 25. The system of example 23 (as well as subject matter of one or more of any combination of examples 2-24), wherein the catheter device comprises a first lumen distal tip, and wherein the expandable component is axially located beginning at the first lumen distal tip and axially extending to a portion of the first lumen distal region.

Example 26. The system of example 23 (as well as subject matter of one or more of any combination of examples 2-22 and 25), wherein the expandable component includes at least one of a balloon and inflatable compartment.

Example 27. The system of example 23 (as well as subject matter of one or more of any combination of examples 2-22 and 24-26), wherein the expandable component has a preformed shape for expansion or inflation.

Example 28. The system of example 1 (as well as subject matter of one or more of any combination of examples 2-27), wherein the medical imaging system comprises at least one of the following: magnetic resonance imaging systems, computed tomography (CT), fluoroscopy, ultrasound, PET scanning, nuclear medicine camera, other radiological systems, or other biomedical imaging systems.

Example 29. The system of example 1 (as well as subject matter of one or more of any combination of examples 2-28), wherein the catheter device is adapted to be visible on a medical imaging system.

Example 30. The system of example 29 (as well as subject matter of one or more of any combination of examples 2-28), wherein the medical imaging system comprises at least one of the following: magnetic resonance imaging systems, computed tomography (CT), fluoroscopy, ultrasound, PET scanning, nuclear medicine camera, other radiological systems, or other biomedical imaging systems.

Example 31. The system of example 1 (as well as subject matter of one or more of any combination of examples 2-30), further comprising: a medical imaging system; and wherein the catheter device is adapted to be visible on the medical imaging system.

Example 32. The system of example 31 (as well as subject matter of one or more of any combination of examples 2-30), wherein the medical imaging system comprises at least one of the following:magnetic resonance imaging system, computed tomography (CT) system, fluoroscopy system, ultrasound system, PET scanning system, nuclear medicine camera system other radiological system, or other biomedical imaging system.

Example 33. An aspect of an embodiment of the present invention provides, but not limited thereto, a method for delivering a diagnostic agent to a site in the brain of a subject for imaging at least a portion of the brain site on a medical imaging system. The method may comprise: providing a catheter device, the catheter device includes as a first lumen, the first lumen having a first lumen proximal region, a first lumen distal regional, and a first lumen longitudinal region there between; at least of a portion of the first lumen having one or more diagnostic agent ports; delivering the diagnostic agent through the first lumen; advancing the diagnostic agent from the first lumen to exit out from the first lumen to at least a portion of the brain site; sealing a portion of the brain site, wherein the sealing prevents the exited diagnostic agent from travelling proximally beyond the sealing location; and imaging at least a portion of the brain site during at least a portion of the sealing duration so that the at least a portion of the brain site can be visualized on a medical imaging system.

Example 34. The method of example 33, wherein the first lumen diagnostic agent comprises: autologous cerebrospinal fluid (CSF).

Example 35. The method of example 33 (as well as subject matter of one or more of any combination of example 34), wherein the first lumen diagnostic agent comprises: artificial cerebrospinal fluid (CSF).

Example 36. The method of example 33 (as well as subject matter of one or more of any combination of examples 34-35), wherein the first lumen diagnostic agent comprises: saline.

Example 37. The method of example 33 (as well as subject matter of one or more of any combination of examples 34-36), wherein the first lumen diagnostic agent comprises an aqueous fluid.

Example 38. The method of example 37 (as well as subject matter of one or more of any combination of examples 34-36), wherein the aqueous fluid comprises at least one of the following: lactated ringers, Dextran, Gadolinium diethylenetriamine penta-acetic acid (DTPA), Gadolinium-albumin, Phosphate Buffered Saline, and Albumin.

Example 39. The method of example 33 (as well as subject matter of one or more of any combination of examples 34-37), further comprising advancing at least one of the following into the first lumen: stylet, electrical lead, ancillary catheter, solid state sensor, electrical conductor, sampling tube, abrading tip, optical fiber, deep brain simulation (DBS) device, or pH sensor.

Example 40. The method of example 33 (as well as subject matter of one or more of any combination of examples 34-39), wherein the catheter device comprises a first lumen distal tip, and the one or more diagnostic agent ports is located at the distal tip of the first lumen.

Example 41. The method of example 40 (as well as subject matter of one or more of any combination of examples 34-39), wherein additional the one or more diagnostic agent ports is located on the wall of the first lumen located at the first lumen distal region.

Example 42. The method of example 33 (as well as subject matter of one or more of any combination of examples 34-41), wherein the one or more diagnostic agent ports is located on the wall of the first lumen located at the first lumen distal region.

Example 43. The method of example 42 (as well as subject matter of one or more of any combination of examples 34-42), wherein the one or more diagnostic agent ports comprises a plurality or array of holes or a dialysis-like membrane.

Example 44. The method of example 33 (as well as subject matter of one or more of any combination of examples 34-43), wherein:
the catheter further includes a second lumen, the second lumen having a second lumen proximal region, a second lumen distal regional, and a second lumen longitudinal region there between; delivering the second lumen agent through the second lumen; and advancing the second lumen agent from the second lumen to exit out from the second lumen to at least a portion of the brain site.

Example 45. The method of 44 (as well as subject matter of one or more of any combination of examples 34-43), further comprising: sealing a portion of the brain site, wherein the sealing prevents the second lumen agent from travelling proximally beyond the sealing location.

Example 46. The method of example 44 (as well as subject matter of one or more of any combination of examples 34-45), wherein the second lumen agent comprises: one or more therapeutic agents.

Example 47. The method of example 44 (as well as subject matter of one or more of any combination of examples 34-46), wherein the second lumen agent comprises: one or more diagnostic agents.

Example 48. The method of example 44 (as well as subject matter of one or more of any combination of examples 34-47), further comprising advancing at least one of the following into the second lumen: stylet, electrical lead, ancillary catheter, solid state sensor, electrical conductor, sampling tube, abrading tip, optical fiber, deep brain simulation (DBS) device, or pH sensor.

Example 49. The method of example 44 (as well as subject matter of one or more of any combination of examples 34-43 and 45-48), wherein the brain site includes the parenchyma.

Example 50. The method of example 44, wherein the brain site includes within the cerebrovasculature.

Example 51. The method of example 33 (as well as subject matter of one or more of any combination of examples 34-50), where the method further comprises:
 the catheter further comprising a third lumen, the third lumen having a third lumen proximal region, a third lumen distal regional, and a third lumen longitudinal region there between; and providing a third lumen material or device through the third lumen.

Example 52. The method of example 51 (as well as subject matter of one or more of any combination of examples 34-50), wherein the third lumen device comprises one of the following: stylet, electrical lead, ancillary catheter, solid state sensor, electrical conductor, sampling tube, abrading tip, optical fiber, or pH sensor.

Example 53. The method of example 51 (as well as subject matter of one or more of any combination of examples 34-50 and 52), wherein the third lumen material comprises one of the following: one or more diagnostic agents and one more therapeutic agents.

Example 54. The method of example 33 (as well as subject matter of one or more of any combination of examples 34-53), wherein the sealing includes expanding an expandable component.

Example 55. The method of example 54 (as well as subject matter of one or more of any combination of examples 34-53), wherein the expandable component includes at least one of a balloon and inflatable compartment.

Example 56. The method of example 54 (as well as subject matter of one or more of any combination of examples 34-55), wherein the expandable component has a pre-formed shape for expansion or inflation.

Example 57. The method of example 33 (as well as subject matter of one or more of any combination of examples 34-56), wherein the sealing occurs at a portion of the first lumen distal region.

Example 58. The method of example 33 (as well as subject matter of one or more of any combination of examples 34-57), wherein the catheter device comprises a first lumen distal tip, and wherein the sealing occurs axially located beginning at the first lumen distal tip and axially extending to a portion of the first lumen distal region.

Example 59. The method of example 33 (as well as subject matter of one or more of any combination of examples 34-58), wherein the imaging comprises at least one of the following: magnetic resonance imaging, computed tomography (CT), fluoroscopy, ultrasound, PET scanning, nuclear medicine camera, other radiological systems, or other biomedical imaging.

Example 60. The method of example 33 (as well as subject matter of one or more of any combination of examples 34-59), further comprising imaging at least a portion of the catheter device.

Example 61. The method of example 60 (as well as subject matter of one or more of any combination of examples 34-59), wherein the imaging of at least a portion of the catheter device comprises at least one of the following: magnetic resonance imaging, computed tomography (CT), fluoroscopy, ultrasound, PET scanning, nuclear medicine camera, other radiological systems, or other biomedical imaging methods.

Example 62. An aspect of an embodiment of the present invention provides, but not limited thereto, a catheter system for delivering a diagnostic agent to a site in the brain of a subject for imaging at least a portion of the brain site on a medical imaging system for purpose of treating a neurologic disorder of the subject. The catheter system may comprise: a catheter device, the catheter device includes as a first lumen, the first lumen having a first lumen proximal region, a first lumen distal regional, and a first lumen longitudinal region there between; the first lumen configured to convey a diagnostic agent within the first lumen, and at least a portion of the first lumen having one or more ports configured to allow the conveyed diagnostic agent to exit from the first lumen to at least a portion of the brain site; a portion of the catheter device having a cross-sectional area greater than portions of the catheter located proximally so as to define a seal within at least a portion of the brain site, wherein the seal is configured to prevent the exited diagnostic agent from travelling proximally beyond the seal while at least a portion of the brain site can be visualized on a medical imaging system; and an electrical lead or deep brain simulation (DBS) device at least partially disposed in the first lumen for applying electrical stimulation by use of the electrical lead or DBS, to a site in the brain for providing a DBS.

Example 63. The system of example 62 (as well as subject matter of one or more of any combination of examples 1-32 and 33-61), wherein the neurologic disorder comprises at least one of the following: Parkinson's disease, tremor, epilepsy, neurodegenerative conditions or diseases, Alzheimer's, seizures, paralysis, or psychiatric disease.

Example 64. An aspect of an embodiment of the present invention provides, but not limited thereto, a catheter system for delivering a diagnostic agent to a site in the brain of a subject for imaging at least a portion of the brain site on a medical imaging system for purpose of treating a neurologic disorder of the subject. The catheter system may comprise: a catheter device, the catheter device includes as a first lumen, the first lumen having a first lumen proximal region, a first lumen distal regional, and a first lumen longitudinal region there between; the first lumen configured to convey a diagnostic agent within the first lumen, and at least a portion of the first lumen having one or more ports configured to allow the conveyed diagnostic agent to exit from the first lumen to at least a portion of the brain site; a portion of the catheter device having a cross-sectional area greater than portions of the catheter located proximally so as to define a seal within at least a portion of the brain site, wherein the seal is configured to prevent the exited diagnostic agent from travelling proximally beyond the seal while at least a portion of the brain site can be visualized on a medical imaging system; a second lumen, the second lumen having a second lumen proximal region, a second lumen distal regional, and a second lumen longitudinal region there between; and an electrical lead or deep brain simulation (DBS) device at least partially disposed in the second lumen for applying electrical stimulation by use of the electrical lead or DBS, to a site in the brain for providing a DBS.

Example 65. The system of example 64 (as well as subject matter of one or more of any combination of examples 1-32 and 33-61), wherein the neurologic disorder comprises at least one of the following: Parkinson's disease, tremor, epilepsy, neurodegenerative conditions or diseases, Alzheimer's, seizures, paralysis, or psychiatric disease.

Example 66. An aspect of an embodiment of the present invention provides, but not limited thereto, a method for delivering a diagnostic agent to a site in the brain of a subject for imaging at least a portion of the brain site on a medical imaging system for purpose of treating a neurologic disorder of the subject, the method comprising: providing a catheter device, the catheter device includes as a first lumen, the first lumen having a first lumen proximal region, a first lumen distal regional, and a first lumen longitudinal region there between; at least of a portion of the first lumen having one or more diagnostic agent ports; delivering the diagnostic agent through the first lumen; advancing the diagnostic agent from the first lumen to exit out from the first lumen to at least a portion of the brain site; sealing a portion of the brain site, wherein the sealing prevents or mitigates (or hinders) the exited diagnostic agent from travelling proximally beyond the sealing location; imaging at least a portion of the brain site during at least a portion of the sealing duration so that the at least a portion of the brain site can be visualized on a medical imaging system; delivering an electrical lead or deep brain simulation (DBS) device into the first lumen; and applying electrical stimulation by use of the electrical lead or DBS, to a site in the brain for providing the DBS.

Example 67. The method of example 66 (as well as subject matter of one or more of any combination of examples 1-32 and 33-61), wherein the neurologic disorder comprises at least one of the following: Parkinson's disease, tremor, epilepsy, neurodegenerative conditions or diseases, Alzheimer's, seizures, paralysis, or psychiatric disease.

Example 68. An aspect of an embodiment of the present invention provides, but not limited thereto, a method for delivering a diagnostic agent to a site in the brain of a subject for imaging at least a portion of the brain site on a medical imaging system for purpose of treating a neurologic disorder of the subject. The method may comprise: providing a catheter device, the catheter device includes as a first lumen, the first lumen having a first lumen proximal region, a first lumen distal regional, and a first lumen longitudinal region there between; at least of a portion of the first lumen having one or more diagnostic agent ports; delivering the diagnostic agent through the first lumen; advancing the diagnostic agent from the first lumen to exit out from the first lumen to at least a portion of the brain site; sealing a portion of the brain site, wherein the sealing prevents the exited diagnostic agent from travelling proximally beyond the sealing location; imaging at least a portion of the brain site during at least a portion of the sealing duration so that the at least a portion of the brain site can be visualized on a medical imaging system; the catheter further includes a second lumen, the second lumen having a second lumen proximal region, a second lumen distal regional, and a second lumen longitudinal region there between; delivering an electrical lead or deep brain simulation (DBS) device into the second lumen; and applying electrical stimulation by use of the electrical lead or DBS, to a site in the brain for providing the DBS.

Example 69. The method of example 68 (as well as subject matter of one or more of any combination of examples 1-32 and 33-61), wherein the neurologic disorders may comprise at least one of the following: Parkinson's disease, tremor, epilepsy, neurodegenerative conditions or diseases, Alzheimer's, seizures, paralysis, or psychiatric disease.

Example 70. The method and system of using any of the aspects of the subject matter found in one or more of any combination of examples 1-61.

Example 71. The method and system of using any of the aspects of the subject matter found in one or more of any combination of examples 1-69.

Example 72. The method of manufacture (using available techniques and materials) to produce any of the systems (or portions thereof) of aspects of the subject matter found in one or more of any combination of examples 1-31 and 62-65

The devices, systems, materials, compositions, and methods of various embodiments of the invention disclosed herein may utilize aspects disclosed in the following references, applications, publications and patents and which are hereby incorporated by reference herein in their entirety (and which are not admitted to be prior art with respect to the present invention by inclusion in this section). Moreover, the multi-lumen techniques and designs, imaging related methods and systems (including but not limited thereto magnetic resonance imaging (MRI), magnetic stereotaxis systems (MSS)), transfer methods and designs for medium, drug, material transfer through the catheter and lumens (including delivery and/or withdrawal), port hole(s) designs and use, balloon(s) (expandable components) designs and use, medium communication and control, operator, user and clinician interface, computer systems, non-transitory computer readable medium, and convection enhanced delivery (CED) methods and systems as disclosed herein may utilize aspects disclosed in the following references, applications, publications and patents and which are hereby incorporated by reference herein in their entirety (and which are not admitted to be prior art with respect to the present invention by inclusion in this section).

1. U.S. patent application Ser. No. 13/704,782 entitled "METERS FOR IN-VIVO MONITORING," filed Jul. 30, 2013.

2. International Patent Application No. PCT/US2011/040976 entitled "METERS FOR IN-VIVO MONITORING," filed Jun. 17, 2011.

3. U.S. patent application Ser. No. 13/780,207 entitled "System and Method for Magnetic Control of an Anesthetic," filed Feb. 28, 2013.

4. U.S. patent application Ser. No. 13/607,993 entitled "Access Needle Pressure Sensor Device and Method of Use," filed Sep. 10, 2012; U.S. Patent Application Publication No. US-2012-0330184, Dec. 27, 2012.

5. U.S. patent application Ser. No. 12/530,830 entitled "Access Needle Pressure Sensor Device and Method of Use," filed Sep. 11, 2009.

6. International Patent Application No. PCT/US2008/056643 entitled "Access Needle Pressure Sensor Device and Method of Use," filed Mar. 12, 2008.

7. U.S. patent application Ser. No. 13/579,745 entitled "ACCESS SYSTEM FOR FEMORAL VASCULATURE CATHETERIZATION AND RELATED METHOD," filed Aug. 17, 2012.

8. International Patent Application No. PCT/US2010/061413 entitled "ACCESS SYSTEM FOR FEMORAL VASCULATURE CATHETERIZATION AND RELATED METHOD," filed Dec. 21, 2010.

9. U.S. patent application Ser. No. 13/579,882 entitled "SYSTEM, METHOD, AND COMPUTER PROGRAM PRODUCT FOR SIMULATING EPICARDIAL ELECTROPHYSIOLOGY PROCEDURES," filed Aug. 17, 2012.

10. International Patent Application No. PCT/US2011/025470 entitled "SYSTEM, METHOD, AND COMPUTER PROGRAM PRODUCT FOR SIMULATING EPICARDIAL ELECTROPHYSIOLOGY PROCEDURES," filed Feb. 18, 2011; U.S. Patent Application Publication No. WO 2011/103456, Aug. 25, 2011.

11. U.S. patent application Ser. No. 13/559,008 entitled "Blood Flow Bypass Catheters and Methods for the Delivery of Medium to the Vasculature and Body Ducts," filed Jul. 26, 2012.

12. U.S. patent application Ser. No. 12/625,153 entitled "Blood Flow Bypass Catheters and Methods for the Delivery of Medium to the Vasculature and Body Ducts," filed Nov. 24, 2009; U.S. Pat. No. 8,255,193, issued Aug. 28, 2012.

13. U.S. patent application Ser. No. 11/884,421 entitled "Blood Flow Bypass Catheters and Methods for the Delivery of Medium to the Vasculature and Body Ducts," filed Aug. 15, 2007.

14. International Patent Application No. US2006/005876 entitled "Blood Flow Bypass Catheters and Methods for the Delivery of Medium to the Vasculature and Body Ducts," filed Feb. 16, 2006.

15. U.S. patent application Ser. No. 13/540,348 entitled "Coaxial Catheter Systems for Transference of Medium," filed Jul. 2, 2012; U.S. Patent Application Publication No. 2013/0090556, Apr. 11, 2013.

16. U.S. patent application Ser. No. 12/760,837 entitled "Coaxial Catheter Systems for Transference of Medium," filed Apr. 15, 2010; U.S. Pat. No. 8,211,083, issued Jul. 3, 2012.

17. U.S. patent application Ser. No. 11/191,676 entitled "Coaxial Catheter Systems for Transference of Medium," filed Jul. 28, 2005; U.S. Pat. No. 7,727,225, issued Jun. 1, 2010.

18. International Patent Application No. PCT/US2005/026738 entitled "Coaxial Catheter Systems for Transference of Medium," filed Jul. 28, 2005.

19. U.S. patent application Ser. No. 13/464,762 entitled "SYSTEMS AND METHODS FOR DETERMINING LOCATION OF AN ACCESS NEEDLE IN A SUBJECT," filed May 4, 2012; U.S. Patent Application Publication No. US-2012-0283582-A1, Nov. 8, 2012.

20. U.S. patent application Ser. No. 13/464,752 entitled "SYSTEMS AND METHODS FOR DETERMINING LOCATION OF AN ACCESS NEEDLE IN A SUBJECT," filed May 4, 2012; U.S. Patent Application Publication No. US-2012-0310052-A1, Dec. 6, 2012.

21. U.S. patent application Ser. No. 13/318,450 entitled "ACCESS TROCAR AND RELATED METHOD THEREOF," filed Nov. 1, 2011.

22. International Patent Application No. PCT/US2010/033189 entitled "ACCESS TROCAR AND RELATED METHOD THEREOF," filed Apr. 30, 2010.

23. U.S. patent application Ser. No. 12/741,710 entitled "STEERABLE EPICARDIAL PACING CATHETER SYSTEM PLACED VIA THE SUBXIPHOID PROCESS," filed May 6, 2010; U.S. Patent Application Publication No. 2010/0241185, Sep. 23, 2010.

24. International Patent Application No. PCT/US2008/082835 entitled "STEERABLE EPICARDIAL PACING CATHETER SYSTEM PLACED VIA THE SUBXIPHOID PROCESS," filed Nov. 7, 2008.

25. U.S. patent application Ser. No. 12/513,258 entitled "Means and Methods for Cytometric Therapies," filed Mar. 17, 2010; U.S. Patent Application Publication No. 2010/0210927, Aug. 19, 2010.

26. International Patent Application No. PCT/US2007/023047 entitled "Means and Methods for Cytometric Therapies," filed Nov. 1, 2007.

27. International Patent Application No. US2006/005876 entitled "Blood Flow Bypass Catheters and Methods for the Delivery of Medium to the Vasculature and Body Ducts," filed Feb. 16, 2006.

28. U.S. patent application Ser. No. 12/532,233 entitled "Electrode Catheter for Ablation Purposes and Related Method Thereof," filed Sep. 21, 2009; U.S. Patent Application Publication No. 2010/0211064, Aug. 19, 2010.

29. International Patent Application No. PCT/US2008/057626 entitled "Electrode Catheter for Ablation Purposes and Related Method Thereof," filed Mar. 20, 2008.

30. U.S. patent application Ser. No. 12/530,938 entitled "Epicardial Ablation Catheter and Method of Use," filed Sep. 11, 2009; U.S. Patent Application Publication No. 2010/0114093, May 6, 2010.

31. International Patent Application No. PCT/US2008/056816 entitled "Epicardial Ablation Catheter and Method of Use," filed Mar. 13, 2008.

32. U.S. patent application Ser. No. 12/304,801 entitled "Closure Device for Skull Plates and Related Method Thereof," filed May 18, 2009; U.S. Pat. No. 8,226,694, issued Jul. 24, 2012.

33. International Patent Application No. PCT/US2007/014881 entitled "Closure Device for Skull Plates and Related Method Thereof," filed Jun. 26, 2007.

34. U.S. patent application Ser. No. 12/375,139 entitled "System and Method for Intracranial Implantation of Therapeutic or Diagnostic Agents," filed Jan. 27, 2009; U.S. Patent Application Publication No. 2009/0192487, Jul. 30, 2009.

35. International Patent Application No. PCT/US2007/016256 entitled "System and Method for Intracranial Implantation of Therapeutic or Diagnostic Agents," filed Jul. 18, 2007.

36. U.S. patent application Ser. No. 12/160,378 entitled "Multi-Port Catheter System with Medium Control and Measurement Systems for Therapy and Diagnosis Delivery," filed Aug. 1, 2008; U.S. Patent Application Publication No. 2009-0048577, Feb. 19, 2009.

37. International Patent Application No. PCT/US2007/000353 entitled "Multi-Port Catheter System with Medium Control and Measurement Systems for Therapy and Diagnosis Delivery," filed Jan. 9, 2007.

38. International Patent Application No. US2006/013621 entitled "Catheter Systems for Delivery of Agents and Related Method Thereof," filed Apr. 12, 2006.

39. U.S. patent application Ser. No. 11/105,166 entitled "Catheter Systems for Delivery of Agents and Related Method Thereof," filed Apr. 13, 2005; U.S. Pat. No. 7,670,327, issued Mar. 2, 2010.

40. U.S. patent application Ser. No. 10/985,340 entitled "Catheter Navigation Within an MR Imaging Device," filed Nov. 10, 2004.

41. U.S. patent application Ser. No. 10/429,524 entitled "Catheter Navigation Within an MR Imaging Device," filed May 5, 2003; U.S. Pat. No. 6,834,201, issued Dec. 21, 2004.

42. International Patent Application No. US02/02363 entitled "Catheter Navigation within an MR Imaging Device," filed Jan. 28, 2002.

43. U.S. patent application Ser. No. 09/772,188 entitled "Catheter Navigation within an MR Imaging Device," filed Jan. 29, 2001.

44. U.S. patent application Ser. No. 10/444,884 entitled "Cell Delivery Catheter and Method," filed May 23, 2003; U.S. Pat. No. 8,096,984, issued Jan. 17, 2012.

45. U.S. patent application Ser. No. 09/574,857 entitled "Cell Delivery Catheter and Method," filed May 19, 2000; U.S. Pat. No. 6,599,274, issued Jul. 29, 2003.

46. U.S. patent application Ser. No. 09/859,472 entitled "Continuous Metal Fiber Brushes," filed May 18, 2001.

47. U.S. patent application Ser. No. 09/147,100 entitled "Continuous Metal Fiber Brushes," filed Apr. 4, 1997; U.S. Pat. No. 6,245,440, issued Jun. 12, 2001.

48. International Patent Application No. US97/05149 entitled "CONTINUOUS METAL FIBER BRUSHES," filed Apr. 4, 1997.

49. U.S. patent application Ser. No. 09/548,110 entitled "Multi-Probe System," filed Apr. 12, 2000; U.S. Pat. No. 6,626,902, issued Sep. 30, 2003.

50. International Patent Application No. US99/24253 entitled "MRI AND MAGNETIC STEREOTAXIS SURGICAL SYSTEM," filed Oct. 15, 1999

51. U.S. patent application Ser. No. 09/174,189 entitled "Combined Magnetic Resonance Imaging and Magnetic Stereotaxis Surgical Apparatus and Processes," filed Oct. 16, 1998; U.S. Pat. No. 6,298,259, issued Oct. 2, 2001.

52. International Patent Application No. US99/17880 entitled "MR-Visible Device for Magnetic Stereotaxis Neurological Interventions," filed Aug. 6, 1999.

53. U.S. patent application Ser. No. 09/131,031 entitled "MR-Visible Medical Device for Neurological Interventions Using Nonlinear Magnetic Stereotaxis and a Method Imaging," filed Aug. 7, 1998;

54. U.S. Pat. No. 6,272,370, issued Aug. 7, 2001.

55. U.S. patent application Ser. No. 09/114,414 entitled "Magnetic Stereotactic System for Treatment Delivery," filed Jul. 13, 1998.

56. U.S. patent application Ser. No. 08/464,279 entitled "Magnetic Stereotactic System for Treatment Delivery," filed Jun. 5, 1995; U.S. Pat. No. 5,707,335, issued Jan. 13, 1998.

57. U.S. patent application Ser. No. 08/096,214 entitled "Magnetic Stereotactic System for Treatment Delivery," filed Jul. 19, 1993; U.S. Pat. No. 5,779,694, issued Jul. 14, 1998.

58. U.S. Patent Application Ser. No. 07/904,032 entitled "MAGNETIC STEREOTACTIC SYSTEM FOR TREATMENT DELIVERY," filed Jun. 25, 1992.

59. U.S. patent application Ser. No. 07/463,340 entitled "Magnetic Stereotactic System for Treatment Delivery," filed Jan. 10, 1990.

60. U.S. Pat. No. 7,371,225 B2, Oldfield, et al., "Method for Convection Enhanced Delivery of Therapeutic Agents", May 13, 2008.

61. U.S. Patent Application Publication No. US 2012/0116360 A1, Sah, et al., "Treatment of Neurological Disorders", May 10, 2012.

62. U.S. Patent Application Publication No. US 2009/0011980 A1, Gill, S., "Method of Treating Parkinson's Disease in Humans by Direct Infusion of Glial Cell-Line Derived Neurotrophic Factor into the Zona Incerta", Jan. 8, 2009.

63. U.S. Pat. No. 6,026,316, Kucharczyk, et al., "Method and Apparatus for use with MR Imaging", Feb. 15, 2000.

64. U.S. Patent Application Publication No. US 2005/0137578 A1, Heruth, et al., "Catheters Incorporating Valves and Permeable Membranes", Jun. 23, 2005.

65. Chen, Zhi-Jian, et al., "A realistic brain tissue phantom for intraparenchymal infusion studies", J. Neurosurgery 101: 314-322, 2004.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A catheter system for delivering a diagnostic agent to a site in the brain of a subject for imaging at least a portion of the brain site on a medical imaging system for purpose of treating a neurologic disorder of the subject, said catheter system comprising:
  a catheter device including a first lumen, said first lumen having a first lumen proximal region, a first lumen distal region, and a first lumen longitudinal region there between;
  said first lumen configured to convey a diagnostic agent within said first lumen, and at least a portion of said first lumen having one or more ports configured to allow the conveyed diagnostic agent to exit from said first lumen to at least a portion of the brain site;
  wherein a portion of said catheter device having a cross-sectional area greater than portions of said catheter located proximally therefrom is configured to define a seal within at least a portion of the brain site, wherein said seal is configured to prevent the exited diagnostic agent from travelling proximally beyond the seal while at least a portion of the brain site can be visualized on a medical imaging system, and wherein the exited diagnostic agent exits distally beyond the seal through the one or more ports, wherein the one or more ports comprise a circumferentially arranged array of holes extending along a length of the first lumen distal region, distally beyond the seal;
  a second lumen, said second lumen having a second lumen proximal region, a second lumen distal region, and a second lumen longitudinal region there between;
  said second lumen configured to convey a second lumen agent within said second lumen, and at least a portion of said second lumen having one or more second lumen agent ports configured to allow the conveyed second lumen agent to exit from said second lumen to at least a portion of the brain site distally beyond the seal;
  wherein said seal is defined such as to prevent the exited second lumen agent from travelling proximally beyond the seal through the one or more second lumen ports, wherein the one or more second lumen ports comprise a circumferentially arranged array of holes extending along a length of the second lumen distal region, distally beyond the seal; and
  an electrical lead or deep brain simulation (DBS) device at least partially disposed in said second lumen for applying electrical stimulation by use of said electrical lead or DBS, to a site in the brain for providing a DBS.

2. The system of claim 1, further comprising:
a first lumen diagnostic agent, wherein said first lumen diagnostic agent comprises:
autologous cerebrospinal fluid (CSF).

3. The system of claim 1, further comprising:
a first lumen diagnostic agent, wherein said first lumen diagnostic agent comprises:
artificial cerebrospinal fluid (CSF).

4. The system of claim 1, further comprising:
a first lumen diagnostic agent, wherein said first lumen diagnostic agent comprises:
saline.

5. The system of claim 1, further comprising:
a first lumen diagnostic agent, wherein said first lumen diagnostic agent comprises an aqueous fluid.

6. The system of claim 5, wherein said aqueous fluid comprises at least one of the following: lactated ringers, Dextran, Gadolinium diethylenetriamine penta-acetic acid (DTPA), Gadolinium-albumin, Phosphate Buffered Saline, and Albumin.

7. The system of claim 1, wherein said one or more ports comprise a dialysis-like membrane.

8. The system of claim 1, further comprising:
a second lumen diagnostic agent, wherein said second lumen agent comprises: one or more therapeutic agents.

9. The system of claim 1, further comprising:
a second lumen diagnostic agent, wherein said second lumen agent comprises: one or more diagnostic agents.

10. The system of claim 1, wherein the second lumen being configured to accommodated at least one of the following: stylet, electrical lead, ancillary catheter, solid state sensor, electrical conductor, sampling tube, abrading tip, optical fiber, deep brain simulation (DBS) device, or pH sensor.

11. The system of claim 1, wherein the second lumen device comprises at least one of the following at least partially disposed therein: stylet, electrical lead, ancillary catheter, solid state sensor, electrical conductor, sampling tube, abrading tip, optical fiber, deep brain simulation (DBS) device, or pH sensor.

12. The system of claim 1, whereby said system for conveying a third lumen material or device, wherein said system further comprises:
a third lumen, said third lumen having a third lumen proximal region, a third lumen distal regional, and a third lumen longitudinal region there between; and
said third lumen configured to convey a third lumen material or device.

13. The system of claim 1, wherein said brain site includes the parenchyma.

14. The system of claim 1, wherein said brain site includes within the cerebrovasculature.

15. The system of claim 12, further comprising:
a third lumen device at least partially disposed therein.

16. The system of claim 15, wherein said third lumen device comprises at least one of the following: stylet, electrical lead, ancillary catheter, solid state sensor, electrical conductor, sampling tube, abrading tip, optical fiber, deep brain simulation (DBS) device, or pH sensor.

17. The system of claim 12, wherein said system further comprises:
a third lumen material at least partially disposed therein.

18. The system of claim 17, wherein said third lumen material comprises at least one of the following: one or more diagnostic agents and one more therapeutic agents.

19. The system of claim 1, wherein the portion of said catheter device having the greater cross-section area includes at least in part an expandable component in communication with said catheter device.

20. The system of claim 19, wherein said expandable component is axially located at a portion of said first lumen distal region.

21. The system of claim 19, wherein said catheter device comprises a first lumen distal tip, and wherein said expandable component is axially located beginning at said first lumen distal tip and axially extending to a portion of said first lumen distal region.

22. The system of claim 19, wherein said expandable component includes at least one of a balloon and inflatable compartment.

23. The system of claim 19, wherein said expandable component has a pre-formed shape for expansion or inflation.

24. The system of claim 1, wherein said medical imaging system comprises at least one of the following: magnetic resonance imaging systems, computed tomography (CT), fluoroscopy, ultrasound, PET scanning, nuclear medicine camera, other radiological systems, or other biomedical imaging systems.

25. The system of claim 1, wherein said catheter device is adapted to be visible on a medical imaging system.

26. The system of claim 25, wherein said medical imaging system comprises at least one of the following: magnetic resonance imaging systems, computed tomography (CT), fluoroscopy, ultrasound, PET scanning, nuclear medicine camera, other radiological systems, or other biomedical imaging systems.

27. The system of claim 1, further comprising:
a medical imaging system; and
wherein said catheter device is adapted to be visible on said medical imaging system.

28. The system of claim 27, wherein said medical imaging system comprises at least one of the following:
magnetic resonance imaging system, computed tomography (CT) system, fluoroscopy system, ultrasound system, PET scanning system, nuclear medicine camera system other radiological system, or other biomedical imaging system.

29. The system of claim 1, wherein said neurologic disorder comprises at least one of the following: Parkinson's disease, tremor, epilepsy, neurodegenerative conditions or diseases, Alzheimer's, seizures, paralysis, or psychiatric disease.

\* \* \* \* \*